United States Patent
Gupta et al.

(10) Patent No.: US 8,932,835 B2
(45) Date of Patent: Jan. 13, 2015

(54) PROCESS FOR THE ENANTIOSELECTIVE ENZYMATIC REDUCTION OF INTERMEDIATES

(75) Inventors: Antje Gupta, Wiesbaden (DE); Maria Bobkova, Wiesbaden (DE); Anke Tschentscher, Eltville-Hattenheim (DE)

(73) Assignee: IEP GmbH, Wiesbaden (DE)

( * ) Notice: Subject to any disclaimer, the term of this patent is extended or adjusted under 35 U.S.C. 154(b) by 667 days.

(21) Appl. No.: 12/680,148

(22) PCT Filed: Sep. 22, 2008

(86) PCT No.: PCT/EP2008/007992
§ 371 (c)(1),
(2), (4) Date: May 17, 2010

(87) PCT Pub. No.: WO2009/040080
PCT Pub. Date: Apr. 2, 2009

(65) Prior Publication Data
US 2010/0248317 A1    Sep. 30, 2010

(30) Foreign Application Priority Data

Sep. 27, 2007 (AT) .............................. A 1530/2007

(51) Int. Cl.
| | |
|---|---|
| C12P 13/00 | (2006.01) |
| C12N 9/02 | (2006.01) |
| C12N 9/04 | (2006.01) |
| C12P 7/02 | (2006.01) |
| C07K 1/20 | (2006.01) |
| C07H 21/04 | (2006.01) |
| C12P 7/04 | (2006.01) |

(52) U.S. Cl.
CPC ........................... *C12P 7/04* (2013.01)
USPC ........... 435/128; 435/189; 435/190; 435/155; 435/280; 530/350; 536/23.2

(58) Field of Classification Search
None
See application file for complete search history.

(56) References Cited

U.S. PATENT DOCUMENTS

| | | | |
|---|---|---|---|
| 5,200,335 A | 4/1993 | Hummel et al. | |
| 5,523,223 A | 6/1996 | Kula et al. | |
| 5,763,236 A | 6/1998 | Kojima et al. | |
| H1893 H | 10/2000 | Patel et al. | |
| 6,645,746 B1 | 11/2003 | Kizaki et al. | |
| 2009/0221044 A1* | 9/2009 | Gupta et al. ................. | 435/135 |
| 2009/0311762 A1 | 12/2009 | Tschentscher et al. | |

FOREIGN PATENT DOCUMENTS

| | | |
|---|---|---|
| AT | 502 395 B1 | 3/2007 |
| DE | 19610984 | 9/1997 |
| DE | 10119274 | 10/2002 |
| DE | 10327454 A1 | 1/2005 |
| JP | 2001-149088 | 6/2001 |
| WO | 02/14528 | 2/2002 |
| WO | 2007/073875 | 7/2007 |
| WO | 2008/068030 | 6/2008 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Ramesh N. Patel, et al "Diastereoselective microbial reduction of (S)-[3-chloro-2-oxo-1(phenylmethyl_propyl]carbamic acid, 1,1-dimethylethyl ester" Tetrahedron: Asymmetry 14 (2003) 3105-3109.
Masaru Wada, et al "Purification and Characterization of NADPH-Dependent Carbonyl Reductase, Involved in Stereoselective Reduction of Ethyl 4-Chloro-3-oxobutanoate, from *Candida* magnolia" Biosci. Bitechnol. Biochem., 62 (2), 280-285, 1998.
Dunming Zhu, et al "Stereoselective Ensymatic Synthesis of Chiral Alcohols with the Use of a Carbonyl Reductase from Candida magnolia with Anti-Prelog Enantioselectivity" J. Org. Chem. 2006, 71, 4202-4205.
Vladimir I. Tishkov, et al "Pilot Scale Production and Isolation of Recombinant NAD+- and NADP+-Specific Formate Dehydrogenases" J. Biotechnol. Bioeng. (1999) 64; 187-193.
Karsten Niefind, et al "Crystallization and preliminary characterizatin of crystals of R-alcohol dehydrogenase from *Lactobacillus brevis*" Crystallization Papers, Acta Cryst (2000) D56, 1696-1698.
Joerg Peters, et al "A novel NADH-dependent carbonyl reductase with an extremely broad substrate range from *Candida parapsilosis*: Purification and characterization" Enzyme Microb. Technol. 1993, vol. 15, November pp. 950-958.

(Continued)

*Primary Examiner* — Iqbal H Chowdhury
(74) *Attorney, Agent, or Firm* — Workman Nydegger

(57) ABSTRACT

A process for the enantioselective enzymatic reduction of a keto compound of general formula I

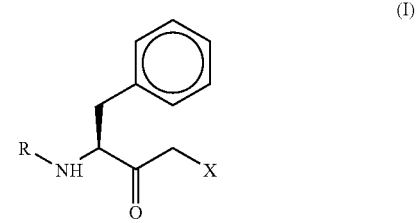

wherein R may represent any protective group for amino functions (tert. butyloxycarbonyl group (BOC), benzyloxycarbonyl group, 9-fluorenylmethoxycarbonyl group) and X=—Cl, —CN, —OH, Br, F.

19 Claims, No Drawings

(56) References Cited

OTHER PUBLICATIONS

Sheng-Xue Xie, et al "NAD+-Dependent (S)-Specific Secondary Alcohol Dehydrogenase Involved in Stereoinversion of 3-Pentyn-2-ol Catalyzed by *Nocardia* fusca AKU 2123" Biosci. Biotechnol. Biochem, 63(10), 1721-1729, 1999.

K. Abokitse, et al "Cloning, sequence analysis, and heterologous expression of the gene encoding a (S)-specific alcohol dehydrogenase from *Rhodococcus erythropolis* DSM 43297" App Microbiol Biotechnol (2003) 62:380-386.

Wolfgang Stampfer, et al "Biocatalytic Asymmetric Hydrogen Transfer Employing *Rhodococcus* ruber DSM 44541" J. Org. Chem. 2003, 68, 402-406.

Molecular cloning: a laboratory manual, 2nd ed., vol. 1, Protocol 32: Hybridization fo BActerial DNA on Fibers, pp. 1.139-1.142 (Cold Spring Harbor Laboratory Press, 1989).

Ramesh N. Patel, et al "Preparation of chiral synthon for HIV protease inhibitor: stereoselective microbial reduction of N-protected α-aminochloroketone" Tetrahedron: Asymmetry, vol. 8, No. 15, pp. 2547-2552, 1997.

* cited by examiner

SEQUENCE LISTING

<160> NUMBER OF SEQ ID NOS: 75

<210> SEQ ID NO 1
<211> LENGTH: 239
<212> TYPE: PRT
<213> ORGANISM: Candida magnoliae

<400> SEQUENCE: 1

```
Met Asn Ala Leu Val Thr Gly Gly Ser Arg Gly Ile Gly Glu Ala Ile
1               5                   10                  15

Ala Thr Lys Leu Ala Glu Asp Gly Tyr Ser Val Thr Ile Ala Ser Arg
            20                  25                  30

Gly Ile Asp Gln Leu Asn Lys Val Lys Ala Lys Leu Pro Val Val Arg
        35                  40                  45

Glu Gly Gln Thr His His Val Trp Gln Leu Asp Leu Ser Asp Ala Glu
    50                  55                  60

Ala Ala Ser Ser Phe Lys Gly Ala Pro Leu Pro Ala Ser Ser Tyr Asp
65                  70                  75                  80

Val Leu Val Asn Asn Ala Gly Val Thr Asp Pro Ser Pro Ile Ala Lys
                85                  90                  95

Gln Ser Asp Ser Glu Ile His Lys Leu Phe Ser Val Asn Leu Leu Ser
            100                 105                 110

Pro Val Ala Leu Thr Lys Thr Tyr Val Gln Ala Val Thr Gly Lys Pro
        115                 120                 125

Arg Glu Thr Pro Ala His Ile Ile Phe Ile Ser Ser Gly Val Ala Ile
    130                 135                 140

Arg Gly Tyr Pro Asn Val Ala Val Tyr Ser Ala Thr Lys Ser Gly Leu
145                 150                 155                 160

Asp Gly Phe Met Arg Ser Leu Ala Arg Glu Leu Gly Pro Glu Gly Val
                165                 170                 175

His Val Asn Thr Val Ser Pro Gly Leu Thr Lys Thr Glu Met Ala Ser
            180                 185                 190

Gly Val Ser Leu Asp Asp Phe Pro Pro Ser Pro Ile Gly Gly Trp Ile
        195                 200                 205

Gln Pro Glu Ala Ile Ala Asp Ala Val Arg Tyr Leu Val Lys Ser Lys
    210                 215                 220

Asn Ile Thr Gly Thr Ile Leu Ser Val Asp Asn Gly Ile Thr Val
225                 230                 235
```

<210> SEQ ID NO 2
<211> LENGTH: 241
<212> TYPE: PRT
<213> ORGANISM: Candida magnoliae

<400> SEQUENCE: 2

```
Met Pro Ser Thr Leu Asn Ala Leu Val Thr Gly Gly Ser Arg Gly Ile
1               5                   10                  15

Gly Glu Ala Thr Ala Val Lys Leu Ala Glu Gly Tyr Gly Ile Thr
            20                  25                  30

Leu Ala Ala Arg Asp Ile Lys Lys Leu Asn Asp Val Lys Ala Lys Leu
        35                  40                  45

Pro Thr Ile Lys Gln Gly Gln Glu His His Val Trp Gln Leu Asp Leu
    50                  55                  60

Ala Asp Val Gln Ala Ala Leu Glu Leu Lys Gly Ala Pro Leu Pro Ala
65                  70                  75                  80

Ser Lys Tyr Asp Leu Leu Val Ala Asn Ala Gly Val Ser Ala His Val
                85                  90                  95

Pro Thr Ala Glu His Asp Asp Ala His Trp Gln Asn Val Ile Thr Ile
            100                 105                 110

Asn Leu Ser Ser Gln Ile Ala Leu Thr Gln Ala Leu Val Arg Ala Ile
        115                 120                 125
```

```
Gly Glu Arg Ser Asp Glu Ala Pro Phe His Ile Val Tyr Val Ser Ser
            130                 135                 140

Ile Ala Ala Leu Arg Gly Asn Pro Met Ser Ala Val Tyr Ser Ala Ser
145                 150                 155                 160

Lys Ala Gly Leu Asp Gly Phe Ala Arg Ser Ile Ser Arg Glu Leu Gly
                165                 170                 175

Pro Lys Gly Ile His Val Asn Thr Val His Pro Gly Leu Thr Lys Thr
            180                 185                 190

Asp Met Thr Val Arg Met Arg Pro Ala Glu Asp Gln Pro Ile Lys Gly
            195                 200                 205

Trp Val Leu Pro Asp Ala Ile Ala Asp Ala Val Val Phe Leu Ala Lys
210                 215                 220

Ser Lys Asn Ile Thr Gly Thr Asn Ile Val Val Asp Asn Gly Arg Val
225                 230                 235                 240

Val
```

<210> SEQ ID NO 3
<211> LENGTH: 254
<212> TYPE: PRT
<213> ORGANISM: Candida geochares

<400> SEQUENCE: 3

```
Met Ser Ser Val Pro Ala Ser Ser Ser Ser Ser Pro Thr Leu Asn
1               5                   10                  15

Ala Leu Val Thr Gly Ala Ser Arg Gly Ile Gly Glu Ala Thr Ala Ile
                20                  25                  30

Gln Leu Ala Ser Gln Gly Tyr Ser Val Thr Leu Ala Ser Arg Gly Leu
            35                  40                  45

Glu Gln Leu Lys Ala Val Lys Ala Lys Leu Pro Leu Val Arg Gln Gly
        50                  55                  60

Gln Thr His His Val Trp Gln Leu Asp Leu Ala Asp Val Ala Ala Ala
65                  70                  75                  80

Gly Ser Phe Lys Gly Ala Pro Leu Pro Ala Ser Ser Tyr Asp Val Leu
                85                  90                  95

Val Ser Asn Ala Gly Val Ala Leu Phe Ser Pro Ile Gly Asp Gln Ala
                100                 105                 110

Asp Glu Asp Trp Gln Arg Met Leu Ala Val Asn Leu Thr Ser Pro Ile
            115                 120                 125

Ala Leu Thr Lys Ala Leu Val Lys Ala Ile Ala Asp Lys Pro Arg Glu
130                 135                 140

Asn Pro Ala His Ile Ile Phe Val Ser Ser Ala Val Ser Leu Arg Gly
145                 150                 155                 160

Tyr Pro Leu Val Gly Val Tyr Ser Ala Thr Lys Ala Gly Leu Asp Gly
                165                 170                 175

Phe Thr Arg Ser Leu Ala His Glu Leu Gly Pro Lys Arg Ile His Val
            180                 185                 190

Asn Thr Val Asn Pro Gly Leu Thr Lys Thr Glu Met Ala Lys Asp Val
            195                 200                 205

Glu Leu Asp Ser Phe Gly Gly Asn Val Pro Ile Ser Gly Trp Ile Gln
        210                 215                 220

Val Asp Ala Ile Ala Asp Ala Val Ser Phe Leu Val Asn Ser Lys Asn
225                 230                 235                 240

Ile Thr Gly Thr Ser Leu Val Val Asp Asn Gly Ile Ser Val
                245                 250
```

<210> SEQ ID NO 4
<211> LENGTH: 239
<212> TYPE: PRT
<213> ORGANISM: Candida magnoliae

<400> SEQUENCE: 4

Met Asn Ala Leu Val Thr Gly Gly Ser Arg Gly Ile Gly Glu Ala Thr
1               5                   10                  15

Ala Ile Gln Leu Ala Gln Glu Gly Tyr Gly Val Thr Leu Val Ala Arg
            20                  25                  30

Gly Ala Arg Gln Leu Asn Glu Val Leu Ala Lys Leu Pro Val Val Arg
        35                  40                  45

Asp Gly Gln Thr His His Ile Trp Gln Leu Asp Leu Ser Asp Pro Glu
    50                  55                  60

Ala Ala Ala Ala Phe Arg Gly Ala Pro Leu Pro Ala Ser Ser Tyr Asp
65                  70                  75                  80

Val Leu Ile Asn Asn Ala Gly Val Ser Ser Leu Ser Pro Phe Val Ala
                85                  90                  95

Gln Ser Asp Glu Val Gln Lys Thr Ile Leu Ala Val Asn Leu Leu Ser
            100                 105                 110

Pro Ile Ala Leu Thr Lys Ala Phe Val Lys Ala Ala Val Gly Lys Pro
        115                 120                 125

Arg Glu Arg Pro Ala His Ile Ile Phe Ile Ser Ser Gly Ala Ala Leu
    130                 135                 140

Arg Gly Phe Ala Asn Met Ala Val Tyr Ser Ala Thr Lys Gly Gly Leu
145                 150                 155                 160

Asp Ser Phe Met Arg Ser Leu Ala Arg Glu Leu Gly Pro Gln Gly Ile
                165                 170                 175

His Val Asn Ser Val Asn Pro Gly Phe Thr Glu Thr Glu Met Thr Ala
            180                 185                 190

Thr Thr Asp Leu Asn Asp Tyr Pro Pro Thr Pro Ile Glu Gly Trp Ile
        195                 200                 205

Gln Pro Arg Ala Ile Ala Asp Ala Ile Leu Phe Leu Leu Lys Ser Arg
    210                 215                 220

Asn Ile Thr Gly Thr Asn Val Thr Val Asp Asn Gly Ile Thr Val
225                 230                 235

<210> SEQ ID NO 5
<211> LENGTH: 249
<212> TYPE: PRT
<213> ORGANISM: Rubrobacter xylanophilus

<400> SEQUENCE: 5

Met Leu Glu Gly Lys Val Ala Val Ile Thr Gly Ala Gly Ser Gly Ile
1               5                   10                  15

Gly Arg Ala Thr Ala Leu Arg Phe Ala Arg Glu Gly Ala Arg Val Val
            20                  25                  30

Val Ala Glu Leu Asp Glu Arg Arg Gly Glu Val Val Arg Glu Ile
        35                  40                  45

Leu Glu Ser Gly Gly Glu Ala Val Phe Val Arg Thr Asp Val Ser Glu
    50                  55                  60

Phe Glu Gln Val Glu Ala Ala Val Glu Arg Ala Val Glu Glu Tyr Gly
65                  70                  75                  80

Thr Leu Asp Val Met Phe Asn Asn Ala Gly Ile Gly His Tyr Ala Pro
                85                  90                  95

```
Leu Leu Glu His Asp Pro Glu His Tyr Asp Arg Val Val Arg Val Asn
            100                 105                 110

Gln Tyr Gly Val Tyr Gly Ile Leu Ala Ala Gly Arg Lys Met Ala
        115                 120                 125

Glu Leu Glu Asn Pro Gly Val Ile Ile Asn Thr Ala Ser Val Tyr Ala
130                 135                 140

Phe Leu Ala Ser Pro Gly Val Ile Gly Tyr His Ala Ser Lys Gly Ala
145                 150                 155                 160

Val Lys Met Met Thr Gln Ala Ala Ala Leu Glu Leu Ala Pro His Gly
                165                 170                 175

Ile Arg Val Val Ala Ile Ala Pro Gly Val Asp Thr Pro Ile Ile
            180                 185                 190

Gln Gly Tyr Lys Asp Met Gly Leu Gly Glu Arg Leu Ala Arg Gly Gln
        195                 200                 205

Met Arg Arg Arg Leu Gln Thr Pro Glu Gln Ile Ala Gly Ala Val Val
210                 215                 220

Leu Leu Ala Thr Glu Glu Ala Asp Ala Ile Asn Gly Ser Val Val Met
225                 230                 235                 240

Thr Asp Asp Gly Tyr Ala Glu Phe Lys
                245
```

<210> SEQ ID NO 6
<211> LENGTH: 250
<212> TYPE: PRT
<213> ORGANISM: Geobacillus kaustophilus

<400> SEQUENCE: 6

```
Met Arg Leu Lys Gly Lys Ala Ala Ile Val Thr Gly Gly Ala Ser Gly
1               5                   10                  15

Ile Gly Arg Ala Thr Ala Ile Arg Phe Ala Glu Glu Gly Ala Lys Val
            20                  25                  30

Ala Val Ser Asp Ile Asn Glu Glu Gly Gly Glu Glu Thr Val Arg Leu
        35                  40                  45

Ile Arg Glu Lys Gly Gly Glu Ala Ile Phe Val Gln Thr Asp Val Ala
    50                  55                  60

Asp Ser Lys Gln Val Ser Arg Leu Val Gln Thr Ala Val Asp Ala Phe
65                  70                  75                  80

Gly Gly Leu His Ile Leu Phe Asn Asn Ala Gly Ile Gly His Ser Glu
                85                  90                  95

Val Arg Ser Thr Asp Leu Ser Glu Glu Glu Trp Asp Arg Val Ile Asn
            100                 105                 110

Val Asn Leu Lys Gly Val Phe Leu Gly Ile Lys Tyr Ala Val Pro Val
        115                 120                 125

Met Lys Gln Cys Gly Gly Gly Ala Ile Val Asn Thr Ser Ser Leu Leu
130                 135                 140

Gly Ile Lys Gly Lys Lys Tyr Glu Ser Ala Tyr Asn Ala Ser Lys Ala
145                 150                 155                 160

Gly Val Ile Leu Leu Thr Lys Asn Ala Ala Leu Glu Tyr Gly Lys Phe
                165                 170                 175

Asn Ile Arg Val Asn Ala Ile Ala Pro Gly Val Ile Asp Thr Asn Ile
            180                 185                 190

Ile Thr Pro Trp Lys Gln Asp Glu Arg Lys Trp Pro Ile Ile Ser Lys
        195                 200                 205

Ala Asn Ala Leu Gly Arg Ile Gly Thr Pro Glu Glu Val Ala Asn Ala
210                 215                 220
```

-continued

Val Leu Phe Leu Ala Ser Asp Glu Ala Ser Phe Ile Thr Gly Ala Thr
225                 230                 235                 240

Leu Ser Val Asp Gly Gly Gly Leu Thr Phe
            245                 250

<210> SEQ ID NO 7
<211> LENGTH: 252
<212> TYPE: PRT
<213> ORGANISM: Chloroflexus aurantiacus

<400> SEQUENCE: 7

Met Glu Pro Pro Phe Ile Gly Lys Val Ala Leu Val Thr Gly Ala Ala
1               5                   10                  15

Ala Gly Ile Gly Arg Ala Ser Ala Leu Ala Phe Ala Arg Glu Gly Ala
            20                  25                  30

Lys Val Val Val Ala Asp Val Asn Val Glu Gly Gly Glu Thr Ile
        35                  40                  45

Ala Leu Cys Arg Ala Leu Asn Thr Asp Ala Met Phe Val Arg Cys Asp
    50                  55                  60

Val Ser Gln Arg Asp Glu Val Glu Arg Leu Ile Ala Leu Ala Val Asp
65                  70                  75                  80

Thr Phe Gly Arg Ile Asp Phe Ala His Asn Asn Ala Gly Ile Glu Gly
                85                  90                  95

Val Gln Ala Met Leu Ala Asp Tyr Pro Glu Val Trp Asp Arg Val
            100                 105                 110

Ile Glu Ile Asn Leu Lys Gly Val Trp Leu Cys Met Lys Tyr Glu Ile
        115                 120                 125

Arg His Met Leu Lys Gln Gly Gly Ala Ile Val Asn Thr Ser Ser
    130                 135                 140

Val Ala Gly Leu Ala Gly Ser Arg Gly Val Ser Ala Tyr Val Ala Ser
145                 150                 155                 160

Lys His Gly Ile Val Gly Ile Thr Lys Ala Ala Ala Leu Glu Tyr Ala
                165                 170                 175

Arg Asn Gly Ile Arg Val Asn Ala Ile Cys Pro Gly Thr Ile His Thr
            180                 185                 190

Ala Met Ile Asp Arg Phe Thr Gln Gly Asp Pro Gln Leu Leu Ala Gln
        195                 200                 205

Phe Ala Glu Gly Glu Pro Ile Gly Arg Leu Gly Ser Pro Glu Glu Val
    210                 215                 220

Ala Asn Ala Val Ile Trp Leu Cys Ser Asp Lys Ala Ser Phe Val Thr
225                 230                 235                 240

Gly Ala Thr Leu Ala Val Asp Gly Gly Arg Leu Ala
                245                 250

<210> SEQ ID NO 8
<211> LENGTH: 241
<212> TYPE: PRT
<213> ORGANISM: Candida magnoliae

<400> SEQUENCE: 8

Met Thr Ser Thr Pro Asn Ala Leu Ile Thr Gly Gly Ser Arg Gly Ile
1               5                   10                  15

Gly Ala Ser Ala Ala Ile Lys Leu Ala Gln Glu Gly Tyr Ser Val Thr
            20                  25                  30

Leu Ala Ser Arg Asp Leu Glu Lys Leu Thr Glu Val Lys Asp Lys Leu
        35                  40                  45

```
Pro Ile Val Arg Gly Gly Gln Lys His Tyr Val Trp Gln Leu Asp Leu
    50                  55                  60

Ala Asp Val Glu Ala Ala Ser Ser Phe Lys Ala Ala Pro Leu Pro Ala
65                  70                  75                  80

Ser Ser Tyr Asp Leu Phe Val Ser Asn Ala Gly Ile Ala Gln Phe Ser
                85                  90                  95

Pro Thr Ala Glu His Thr Asn Ser Glu Trp Leu Asn Ile Met Thr Ile
            100                 105                 110

Asn Leu Val Ser Pro Ile Ala Leu Thr Lys Ala Leu Leu Gln Ala Val
        115                 120                 125

Ser Gly Arg Ser Ser Glu Asn Pro Phe Gln Ile Val Phe Ile Ser Ser
    130                 135                 140

Val Ala Ala Leu Arg Gly Val Ala Gln Thr Ala Val Tyr Ser Ala Ser
145                 150                 155                 160

Lys Ala Gly Thr Asp Gly Phe Ala Arg Ser Leu Ala Arg Glu Leu Gly
                165                 170                 175

Pro Gln Gly Val His Val Asn Val Val Asn Pro Gly Trp Thr Lys Thr
            180                 185                 190

Asp Met Thr Glu Gly Val Glu Thr Pro Lys Met Pro Ile Lys Gly
        195                 200                 205

Trp Ile Gln Pro Glu Ala Ile Ala Asp Ala Val Val Phe Leu Ala Arg
    210                 215                 220

Ser Lys Asn Ile Thr Gly Ala Asn Ile Val Val Asp Asn Gly Phe Ser
225                 230                 235                 240

Thr

<210> SEQ ID NO 9
<211> LENGTH: 241
<212> TYPE: PRT
<213> ORGANISM: Candida magnoliae

<400> SEQUENCE: 9

Met Thr Thr Thr Ser Asn Ala Leu Val Thr Gly Gly Ser Arg Gly Ile
1               5                   10                  15

Gly Ala Ala Ser Ala Ile Lys Leu Ala Gln Glu Gly Tyr Asn Val Thr
                20                  25                  30

Leu Ala Ser Arg Ser Val Asp Lys Leu Asn Glu Val Lys Ala Lys Leu
            35                  40                  45

Pro Ile Val Gln Asp Gly Gln Lys His Tyr Ile Trp Glu Leu Asp Leu
    50                  55                  60

Ala Asp Val Glu Ala Ala Ser Ser Phe Lys Gly Ala Pro Leu Pro Ala
65                  70                  75                  80

Arg Ser Tyr Asp Val Phe Val Ser Asn Ala Gly Val Ala Ala Phe Ser
                85                  90                  95

Pro Thr Ala Asp His Asp Asp Lys Glu Trp Gln Asn Leu Leu Ala Val
            100                 105                 110

Asn Leu Ser Ser Pro Ile Ala Leu Thr Lys Ala Leu Leu Lys Asp Val
        115                 120                 125

Ser Glu Arg Pro Val Asp Lys Pro Leu Gln Ile Ile Tyr Ile Ser Ser
    130                 135                 140

Val Ala Gly Leu His Gly Ala Ala Gln Val Ala Val Tyr Ser Ala Ser
145                 150                 155                 160

Lys Ala Gly Leu Asp Gly Phe Met Arg Ser Val Ala Arg Glu Val Gly
                165                 170                 175
```

```
Pro Lys Gly Ile His Val Asn Ser Ile Asn Pro Gly Tyr Thr Lys Thr
            180                 185                 190

Glu Met Thr Ala Gly Ile Glu Ala Leu Pro Asp Leu Pro Ile Lys Gly
        195                 200                 205

Trp Ile Glu Pro Glu Ala Ile Ala Asp Ala Val Leu Phe Leu Ala Lys
    210                 215                 220

Ser Lys Asn Ile Thr Gly Thr Asn Ile Val Val Asp Asn Gly Leu Ile
225                 230                 235                 240

Ala

<210> SEQ ID NO 10
<211> LENGTH: 252
<212> TYPE: PRT
<213> ORGANISM: Candida magnoliae

<400> SEQUENCE: 10

Met Ser Tyr Gln Met Ser Ser Ala Pro Ser Ser Thr Ser Leu Asn
1               5                   10                  15

Ala Leu Val Thr Gly Gly Ser Arg Gly Ile Gly Glu Ala Thr Ala Ile
            20                  25                  30

Lys Leu Ala Glu Glu Gly Tyr Ser Val Thr Ile Ala Ser Arg Gly Leu
        35                  40                  45

Lys Gln Leu Glu Ala Val Lys Ala Lys Leu Pro Ile Val Lys Gln Gly
    50                  55                  60

Gln Val His His Val Trp Gln Leu Asp Leu Ser Asp Val Asp Ala Ala
65                  70                  75                  80

Ala Ala Phe Lys Gly Ser Pro Leu Pro Ala Ser Arg Tyr Asp Val Leu
                85                  90                  95

Val Ser Asn Ala Gly Val Ala Gln Phe Ser Pro Phe Ile Glu His Ala
            100                 105                 110

Lys Gln Asp Trp Ser Gln Met Leu Ala Ile Asn Leu Ala Ala Pro Ile
        115                 120                 125

Ala Leu Ala Gln Thr Phe Ala Lys Ala Ile Gly Asp Lys Pro Arg Asn
130                 135                 140

Thr Pro Ala His Ile Val Phe Val Ser Ser Asn Val Ser Leu Arg Gly
145                 150                 155                 160

Phe Pro Asn Ile Gly Val Tyr Thr Ala Thr Lys Ala Gly Ile Asp Gly
                165                 170                 175

Phe Met Arg Ser Val Ala Arg Glu Leu Gly Pro Ser Gly Ile Asn Val
            180                 185                 190

Asn Ser Val Asn Pro Gly Pro Thr Arg Thr Glu Met Thr Lys Gly Ile
        195                 200                 205

Asp Val Gly Thr Ile Asp Met Pro Ile Lys Gly Trp Ile Glu Pro Glu
    210                 215                 220

Ala Ile Ala Asp Ala Val Leu Phe Val Val Lys Ser Lys Asn Ile Thr
225                 230                 235                 240

Gly Thr Thr Val Val Val Asp Asn Gly Ser Ser Ala
                245                 250

<210> SEQ ID NO 11
<211> LENGTH: 252
<212> TYPE: PRT
<213> ORGANISM: Candida magnoliae

<400> SEQUENCE: 11
```

```
Met Thr Thr Ser Ser Thr Ser Ser Thr Ser Ser Arg Ser Leu Asn
1               5                   10                  15
Ala Leu Val Thr Gly Ala Ser Arg Gly Ile Gly Glu Ala Thr Ala Ile
            20                  25                  30
Lys Leu Ala Ser Glu Gly Tyr Ser Val Thr Leu Ala Ser Arg Ser Leu
        35                  40                  45
Glu Gln Leu Lys Ala Leu Lys Glu Lys Leu Pro Val Val Lys Gln Gly
    50                  55                  60
Gln Thr His His Val Trp Gln Leu Asp Leu Ser Asp Val Asp Ala Ala
65                  70                  75                  80
Ala Thr Phe Lys Gly Ser Pro Leu Pro Ala Ser Ser Tyr Asp Ala Val
                85                  90                  95
Ile Ser Asn Ala Gly Val Ala Gln Phe Ser Pro Leu Ser Glu His Ala
            100                 105                 110
Arg Glu Asp Trp Ser Gln Met Leu Thr Ile Asn Leu Ala Ala Pro Ile
        115                 120                 125
Ala Leu Ala Gln Ala Phe Val Lys Ala Ile Gly Asp Lys Lys Arg Asp
    130                 135                 140
Ile Pro Ala Gln Ile Val Phe Val Ser Ser Asn Val Val Met Arg Gly
145                 150                 155                 160
Leu Pro Tyr Leu Gly Ile Tyr Thr Ala Ser Lys Ala Gly Ile Asp Gly
                165                 170                 175
Phe Met Arg Ser Ala Ala Arg Glu Leu Gly Pro Lys Gly Ile Asn Val
            180                 185                 190
Asn Ser Val Asn Pro Gly Ala Thr Gln Thr Glu Met Thr Lys Gly Val
        195                 200                 205
Asp Val Asn Ala Leu Asp Leu Pro Ile Lys Gly Trp Ile Gln Leu Glu
    210                 215                 220
Ala Val Ala Asp Ala Val Leu Phe Val Gln Ser Lys Asn Ile Thr
225                 230                 235                 240
Gly Thr Thr Ile Val Val Asp Asn Gly Ser Val Ala
                245                 250

<210> SEQ ID NO 12
<211> LENGTH: 240
<212> TYPE: PRT
<213> ORGANISM: Candida magnoliae

<400> SEQUENCE: 12

Met Asn Ala Leu Val Thr Gly Ala Ser Arg Gly Ile Gly Glu Ala Ile
1               5                   10                  15
Ala Val Lys Leu Ala Glu Asp Gly Tyr Ser Val Thr Leu Ala Ser Arg
            20                  25                  30
Ser Leu Glu Lys Leu Glu Ser Leu Lys Lys Gly Leu Pro Val Val Lys
        35                  40                  45
Asp Gly Gln Ala His His Val Trp Glu Leu Asp Leu Gly Asp Val Asp
    50                  55                  60
Ala Ala Ser Ser Phe Lys Gly Ala Pro Leu Pro Ala Glu Ala Tyr Asp
65                  70                  75                  80
Val Phe Val Ser Asn Ala Gly Met Ala Lys Ser Thr Leu Met Val Asp
                85                  90                  95
His Pro Ile Asp Glu Leu Gln Asp Met Ile Asn Val Asn Leu Val Ser
            100                 105                 110
Pro Ile Ala Leu Thr Gln Gly Leu Val Lys Ala Leu Thr Glu Ser Lys
        115                 120                 125
```

```
Arg Asp Lys Pro Ala His Ile Val Phe Met Ser Ser Ile Arg Ser Phe
        130                 135                 140

Arg Gly Ile Pro Asn Gly Ala Val Tyr Ser Ala Thr Lys Ser Gly Leu
145                 150                 155                 160

Asp Gly Phe Met Arg Ser Ile Ala Arg Glu Leu Gly Pro Gln Gly Ile
                165                 170                 175

His Val Asn Ser Val Cys Pro Gly Phe Val Gln Thr Glu Met Thr Arg
            180                 185                 190

Lys Val Asp Met Glu Ser Lys Lys Asp Gln Leu Pro Ile Ala Gly Trp
        195                 200                 205

Ile Gln Pro Asp Ala Ile Ala Asp Thr Val Leu Phe Phe Val Lys Ser
210                 215                 220

Lys Asn Ile Thr Gly Gln Ala Ile Val Val Asp Asn Gly Ile Thr Val
225                 230                 235                 240

<210> SEQ ID NO 13
<211> LENGTH: 244
<212> TYPE: PRT
<213> ORGANISM: Candida gropengiesseri

<400> SEQUENCE: 13

Met Pro Ser Gly Leu Asn Ala Leu Val Thr Gly Gly Ser Arg Gly Ile
1               5                   10                  15

Gly Ala Ala Ala Ala Thr Lys Leu Ala Ala Gly Tyr Asn Val Thr
                20                  25                  30

Val Ala Ser Arg Gly Val Glu Ala Leu Asn Lys Val Lys Ala Ser Leu
            35                  40                  45

Pro Val Val Lys Glu Gly Gln Gln His His Val Trp Gln Leu Asp Val
    50                  55                  60

Ser Asp Leu Ala Ala Val Ser Gly Phe Lys Gly Ser Pro Leu Pro Ala
65                  70                  75                  80

Lys Ser Tyr Asp Val Val Val Asn Ala Gly Val Ala Asn Leu Ser
                85                  90                  95

Pro Leu Ala Ala Gln Asp Asp Val Ile Gln Asn Ile Val Thr Val
            100                 105                 110

Asn Leu Leu Ser Pro Ile Ala Leu Val Lys Ser Leu Ile Lys Ala Tyr
        115                 120                 125

Gly Glu Gly Pro Arg Ala Thr Pro Ala His Ile Val Phe Val Ser Ser
    130                 135                 140

Val Ala Ala Ile Arg Gly Phe Pro Asn Gly Ala Val Tyr Ser Ser Thr
145                 150                 155                 160

Lys Ser Ala Leu Asp Gly Leu Thr Arg Ser Leu Ala Lys Glu Leu Gly
                165                 170                 175

Pro Gln Asn Ile Arg Val Asn Ser Val Asn Pro Gly Phe Thr Arg Thr
            180                 185                 190

Glu Leu Ala Ser Gly Val Asp Ile Asp Ala Val Thr Gln Ser Ser Pro
        195                 200                 205

Ile Lys Gly Trp Val Glu Pro Glu Ala Ile Gly Asp Ala Ile Leu Phe
    210                 215                 220

Leu Ala Thr Ser Asn His Ile Thr Gly Thr Ile Thr Val Ile Asp Asn
225                 230                 235                 240

Gly Thr Ser Ala

<210> SEQ ID NO 14
```

```
<211> LENGTH: 249
<212> TYPE: PRT
<213> ORGANISM: Candida sp.

<400> SEQUENCE: 14

Met Ser Ser Ser Ser Ser Thr Pro Leu Asn Ala Leu Val Thr Gly
1               5                   10                  15

Ala Ser Arg Gly Ile Gly Glu Val Ile Ser Leu Gln Leu Ala Asn Glu
            20                  25                  30

Gly Tyr Asn Val Thr Leu Ala Ala Arg Ser Leu Asp Asp Leu Asn Ala
            35                  40                  45

Val Lys Ala Lys Leu Pro Ile Val Arg Asp Ala Gln Lys His Ser Val
50                  55                  60

Trp Pro Leu Asp Ile Ser Asp Ile Asp Ala Val Thr Asn Phe Lys Gly
65                  70                  75                  80

Ser Pro Leu Pro Ala Glu Lys Tyr Asp Leu Phe Val Ser Asn Ala Gly
                85                  90                  95

Val Val Asp Phe Ala Pro Leu Val His Gln Ser Pro Glu Ser Ile Ser
                100                 105                 110

Ser Leu Phe Asn Val Asn Leu Ile Ala Pro Val Ala Leu Thr Lys Ala
            115                 120                 125

Leu Leu Lys Ala Phe Gly Asp Ser Pro Arg Lys Thr Thr Thr His Phe
130                 135                 140

Ile Tyr Val Ser Ser Val Ala Leu Arg Gly Phe Pro Asn Val Ala
145                 150                 155                 160

Val Tyr Ser Ser Ser Lys Ser Gly Leu Asp Gly Phe Val Arg Ser Leu
                165                 170                 175

Ala Ala Glu Val Ala Pro Leu Asn Ile Arg Val Asn Ser Ile Asn Pro
            180                 185                 190

Gly Pro Thr Lys Thr Glu Met Thr Ala Ser Leu Asp Val Glu Ala Phe
            195                 200                 205

Thr Ala Gly Asn Pro Ile Lys Gly Trp Ile Tyr Pro Asp Ala Ile Ala
    210                 215                 220

Asp Gly Val Val Tyr Leu Ala Lys Ser Lys Asn Ile Thr Gly Ile Thr
225                 230                 235                 240

Leu Gln Val Asp Asn Gly Ala Gly Ile
                245

<210> SEQ ID NO 15
<211> LENGTH: 241
<212> TYPE: PRT
<213> ORGANISM: Candida vaccinii

<400> SEQUENCE: 15

Met Arg Ser Thr Pro Asn Ala Leu Val Thr Gly Gly Ser Arg Gly Ile
1               5                   10                  15

Gly Ala Ala Ala Ala Ile Lys Leu Ala Glu Ala Gly Tyr Ser Val Thr
            20                  25                  30

Leu Ala Ser Arg Gly Leu Asp Lys Leu Asn Glu Val Lys Ala Lys Leu
        35                  40                  45

Pro Val Val Lys Gln Gly Gln Glu His His Val Trp Gln Leu Asp Leu
50                  55                  60

Ser Asp Val Gln Ala Ala Leu Glu Phe Lys Gly Ala Pro Leu Pro Ala
65                  70                  75                  80

Ser Lys Tyr Asp Leu Phe Val Ser Asn Ala Gly Val Ala Thr Phe Ser
                85                  90                  95
```

```
Pro Thr Ala Glu His Asp Asp Lys Asp Trp Gln Asn Ile Ile Ala Val
            100                 105                 110

Asn Leu Thr Ser Pro Ile Ala Ile Thr Lys Ala Leu Val Lys Ala Val
        115                 120                 125

Gly Glu Arg Ser Asn Asp Asn Pro Phe Gln Ile Ala Phe Leu Ser Ser
130                 135                 140

Ala Ala Ala Leu Arg Gly Val Pro Gln Thr Ala Val Tyr Ser Ala Thr
145                 150                 155                 160

Lys Ala Gly Leu Asp Gly Phe Thr Arg Ser Leu Ala Lys Glu Leu Gly
                165                 170                 175

Pro Lys Gly Ile His Val Asn Ile Val His Pro Gly Trp Thr Gln Thr
            180                 185                 190

Glu Met Thr Ala Gly Val Asp Glu Pro Arg Asp Thr Pro Ile Pro Gly
        195                 200                 205

Trp Ile Gln Pro Glu Ala Ile Ala Glu Ala Ile Val Tyr Leu Ala Lys
    210                 215                 220

Ser Lys Asn Ile Thr Gly Thr Asn Ile Val Val Asp Asn Gly Leu Thr
225                 230                 235                 240

Ile
```

<210> SEQ ID NO 16
<211> LENGTH: 720
<212> TYPE: DNA
<213> ORGANISM: Candida magnoliae

<400> SEQUENCE: 16

```
atgaacgctc tagtgaccgg tggtagccgt ggcattggcg aggcgatcgc gaccaagctg    60
gccgaagatg gctacagcgt gacaatcgcc tcgcgcggaa tcgatcagct caacaaggta   120
aaggctaaac ttccggttgt gagggagggc cagacccacc acgtgtggca gcttgatttg   180
agcgacgccg aggccgcgtc gtccttcaag ggcgctcctt tgccagcaag cagctacgat   240
gtccttgtca caacgccgg agtaacggat ccgagtccca ttgcgaagca gtcggatagc   300
gagattcaca gctgtttag cgtgaatctg ctgtcaccag ttgctttgac aaagacgtac   360
gtccaggcgg ttaccggaaa gcctcgtgag acgccagctc acattatttt tatctcgtca   420
ggcgttgcca ttcgaggcta cccaaacgtc gctgtatact cggctactaa gagcgggctc   480
gacggtttca tgaggtctct ggcgcgcgag cttggccccg agggcgtcca tgtgaacact   540
gtcagcccgg gtctcaccaa aaccgagatg gccagcggcg tcagcctcga cgacttcccg   600
ccatcgccga ttgggggctg gatccagccc gaggccatcg ctgatgcagt gaggtacctg   660
gtgaagtcga gaacatcac aggcacgatt ctgtcagttg acaacggaat cacggtttaa   720
```

<210> SEQ ID NO 17
<211> LENGTH: 726
<212> TYPE: DNA
<213> ORGANISM: Candida magnoliae

<400> SEQUENCE: 17

```
atgccttcta ctctgaacgc tcttgtcact ggcggcagtc gcggtattgg cgaggctacc    60
gcagtgaagc tcgccgagga gggctacggt atcacacttg ctgcgcgcga tatcaaaaaa   120
ctgaatgacg tgaaggccaa actacccaca atcaagcagg tcaagagca ccacgtctgg   180
cagcttgact tggccgatgt gcaggctgcg cttgagctca agggcgcacc actgcctgcg   240
agcaagtacg acctgttggt cgcgaatgcg ggcgtttccg cacacgttcc tacggccgag   300
```

```
cacgacgatg cgcactggca gaacgtcata actatcaact tgagctcgca gattgcgctc    360
acgcaggccc tagttagggc cattggcgag aggtctgatg aagcgccttt ccacattgtg    420
tatgtgtcct cgatcgccgc cctgcgcggt aaccccatga gcgcggtgta cagtgcctcg    480
aaggccggac ttgatggatt tgctcgttcc atctctcgcg agctcggccc gaagggtatt    540
catgtgaata cggtgcaccc gggactcacg aagacggaca tgaccgttcg catgcggcct    600
gctgaggacc agccgatcaa gggctgggta ctgcccgatg caattgctga tgccgttgtg    660
ttcctcgcga agtctaaaaa catcacgggc acaaacatcg ttgtcgacaa cggccgggtg    720
gtctaa                                                               726

<210> SEQ ID NO 18
<211> LENGTH: 726
<212> TYPE: DNA
<213> ORGANISM: Candida geochares

<400> SEQUENCE: 18
atgccttcta ctctgaacgc tcttgtcact ggcggcagtc gcggtattgg cgaggctacc     60
gcagtgaagc tcgccgagga gggctacggt atcacacttg ctgcgcgcga tatcaaaaaa    120
ctgaatgacg tgaaggccaa actacccaca atcaagcagg gtcaagagca ccacgtctgg    180
cagcttgact tggccgatgt gcaggctgcg cttgagctca agggcgcacc actgcctgcg    240
agcaagtacg acctgttggt cgcgaatgcg ggcgtttccg cacacgttcc tacggccgag    300
cacgacgatg cgcactggca gaacgtcata actatcaact tgagctcgca gattgcgctc    360
acgcaggccc tagttagggc cattggcgag aggtctgatg aagcgccttt ccacattgtg    420
tatgtgtcct cgatcgccgc cctgcgcggt aaccccatga gcgcggtgta cagtgcctcg    480
aaggccggac ttgatggatt tgctcgttcc atctctcgcg agctcggccc gaagggtatt    540
catgtgaata cggtgcaccc gggactcacg aagacggaca tgaccgttcg catgcggcct    600
gctgaggacc agccgatcaa gggctgggta ctgcccgatg caattgctga tgccgttgtg    660
ttcctcgcga agtctaaaaa catcacgggc acaaacatcg ttgtcgacaa cggccgggtg    720
gtctaa                                                               726

<210> SEQ ID NO 19
<211> LENGTH: 720
<212> TYPE: DNA
<213> ORGANISM: Candida magnoliae

<400> SEQUENCE: 19
atgaacgcgt tagtgaccgg cggaagccgc gggatcggcg aggccacggc catacagctg     60
gctcaggagg gctacggtgt gacattggtt gcgcgaggag cccgccagct caatgaagtg    120
ttggcaaagc taccagttgt gagagacgga cagacgcacc acatttggca gctagatctg    180
agcgatcctg aggcggccgc tgccttcagg ggtgctcctt tgcccgccag cagctacgac    240
gtgctgatca ataacgcagg tgttagtagt ctcagcccgt tcgtcgcgca gtctgatgag    300
gtccagaaaa ctattttagc ggtgaatctt ttgtcgccaa tcgcgttgac gaaggcgttc    360
gtgaaggcag cggtgggcaa gccgcgtgag aggccggcgc atatcatttt catctcttcg    420
ggcgctgccc tgcgcggttt cgcgaacatg gcagtgtata gtgcaacgaa aggcggcctt    480
gacagtttca tgcgctcgct agctagagag ctaggtcccc agggcatcca cgtcaactca    540
gtcaatccgg gctttactga aacagaaatg acagccacta cagatttgaa tgactacccc    600
```

-continued

```
ccgacccca ttgagggctg gattcagcct cgcgcaatcg ccgacgctat acttttccta      660
ctgaagtcca gaaacatcac tggcacaaat gtgaccgtcg acaacggcat cactgtttga    720
```

<210> SEQ ID NO 20
<211> LENGTH: 750
<212> TYPE: DNA
<213> ORGANISM: Rubrobacter xylanophilus

<400> SEQUENCE: 20

```
atgctcgagg ggaaggtcgc ggtcatcacg ggggccggca gcggcatagg ccgggccacc     60
gcgctcaggt tcgcccgcga aggggcccgg gtggtcgtgg cggagctcga cgagcggagg    120
ggggaggagg tcgtccggga gatcctcgag tccggcgggg aggccgtctt cgtgaggacg    180
gacgtctcgg agttcgagca ggttgaggcc gccgtcgagc gcgccgtcga ggagtacggg    240
acgctggacg tcatgttcaa caacgccggc atcgggcact acgcccccct gctggagcac    300 gaccccggagc actacgaccg ggtggtccgg gtgaaccagt acggcgtcta ctacgggata    360
ctcgccgccg gcaggaagat ggccgagctg gagaaccccg gcgtgatcat caacaccgcc    420
tcggtctacg cttttcctggc ctcccccggt gtgatcggct atcacgcttc caaggggggcg    480 gtgaagatga tgacccaggc cgcagccctg gagctcgccc ccacggcat acgggtcgtc      540 gccatcgccc cgggcggggt ggacaccccg atcatccagg gctacaagga catgggcctc    600
ggtgagcggc tggcccgcgg ccagatgcgt cgcaggctcc agaccccccga gcagatcgcc    660 ggcgccgtcg tcctgctcgc caccgaggag gcagacgcca taaacggctc ggtggtgatg    720
accgacgacg gctacgcgga gttcaagtaa                                      750
```

<210> SEQ ID NO 21
<211> LENGTH: 753
<212> TYPE: DNA
<213> ORGANISM: Gebacillus kaustophilus

<400> SEQUENCE: 21

```
atgaggctaa aaggaaaagc ggcgattgtc accggcggcg cgagcggcat cggccgggcg     60
acggcgattc gctttgcgga agaaggcgcc aaagtggcgg tgagcgacat caatgaggaa    120
ggaggggaag aaacggtccg cctgattcgg gaaaaggag gggaggcgat ttttgtccaa    180
acggacgtag ccgattccaa gcaagtgagc cgccttgtcc aaacggcggt tgatgccttt    240
ggcggcctac atattctctt taacaatgcc ggcatcggcc attcggaagt gcggagcacc    300
gacttgtctg aagaagagtg ggaccgggtc atcaacgtta atttgaaagg agtgttcctt    360
ggcatcaaat acgcggtgcc cgtgatgaag caatgcggtg gcggggccat tgtcaacaca    420
tcgagcctgc ttggaatcaa agggaaaaag tacgaatcgg cctacaacgc ctcgaaggcc    480
ggggtgattt tgttgacgaa aaatgcagca ttggaatatg ggaagtttaa cattcgcgtc    540
aatgccattg caccgggggt cattgatacg aacatcatca cgccgtggaa acaagatgag    600
cgcaaatggc cgatcatttc gaaagcgaac gccctcggcc gcatcgggac gccagaggaa    660
gtggcgaacg cggtgttgtt tttggcgtcc gatgaagcgt cgtttatcac cggcgcgaca    720
ttgtcggtcg acggcggcgg gctgacgttt tag                                  753
```

<210> SEQ ID NO 22
<211> LENGTH: 759
<212> TYPE: DNA
<213> ORGANISM: Chloroflexus aurantiacus

<400> SEQUENCE: 22

```
atggagccac ctttcattgg gaaggttgcg ctggtcaccg gcgcagcagc cggtattggt      60
cgtgcttcag cactggcgtt tgcccgtgag ggtgccaagg ttgtcgttgc tgatgtgaat     120
gtcgagggcg gggaagagac gattgcgctg tgtcgggctt tgaataccga tgcaatgttc     180
gtgcgttgtg atgtttcgca acgcgatgaa gtggagcgat taattgctct ggcagttgac     240
acgttcggtc ggatcgactt tgcgcacaac aacgccggga ttgaaggcgt gcaggcaatg     300
ctggccgatt atcccgaaga ggtctgggat cgggtgatcg agatcaacct caaaggggtc     360
tggttgtgta tgaagtacga aatccggcac atgctcaagc agggtggcgg tgcgattgtg     420
aatacctcat cggtcgccgg tctgccggga tcacgtggcg tttcggcgta tgtagccagc     480
aagcacggta ttgttggtat taccaaagcg gcagcccttg agtatgcgcg taacggtatt     540
cgtgtcaacg caatctgtcc aggtacgatt catactgcga tgatcgaccg ctttacccag     600
ggtgatcccc aactgcttgc ccagttcgct gagggtgaac cgattggtcg gctcggctcg     660
cctgaagagg tcgccaatgc ggtgatctgg ctctgctcag ataaggcttc gtttgtgacc     720
ggagcgacac tggcggttga tggtggccgc ctggcgtaa                            759
```

<210> SEQ ID NO 23
<211> LENGTH: 726
<212> TYPE: DNA
<213> ORGANISM: Candida magnoliae

<400> SEQUENCE: 23

```
atgacatcta cacctaatgc cctcatcacg ggaggcagcc gcggcattgg cgcttccgcc      60
gccatcaaac tggctcaaga agggtacagc gtcacgctgg cgtcccgcga ccttgagaaa     120
cttactgagg tcaaggacaa gctgccaatc gtgagaggtg acagaaaaca ctacgtttgg     180
cagctcgatc ttgccgatgt ggaggctgca tcgtctttca aggcggctcc tctgccggcc     240
agcagctacg atttgtttgt ttcgaacgcc ggaattgccc agttctcgcc tacggcagag     300
catactaata gtgagtggct gaacattatg accattaact agtgtcccc gattgccctg      360 acgaaggctc ttttgcaggc cgtttctggg aggtcgagcg agaacccgtt tcagatcgtc     420
ttcatctcgt cggttgcagc actacgtggc gttgcacaaa cggccgtcta cagtgcgtcg     480
aaggctggta ctgatggatt cgcacgctca cttgctcgcg aactaggtcc tcaaggtgtt     540
catgtgaacg tggtgaaccc tggctggact aagacagaca tgacgaagg agtcgaaacc      600 ccaaaggaca tgcccattaa gggctggatc cagcctgagg caattgctga tgctgtagta     660
ttccttgcga ggtcgaaaaa cattaccggc gcgaatattg tagtggacaa tggtttctcg     720
acgtaa                                                                726
```

<210> SEQ ID NO 24
<211> LENGTH: 726
<212> TYPE: DNA
<213> ORGANISM: Candida magnoliae

<400> SEQUENCE: 24

```
atgacgacta cttcaaacgc gcttgtcact ggaggcagcc gcggcattgg cgctgcctcc      60
gccattaagc tggctcagga gggctacaat gttacgctgg cctctcgcag tgttgataaa     120
ctgaatgaag taaaggcgaa actcccaatt gtacaggacg ggcagaagca ctacatttgg     180
gaactcgatc tggctgatgt ggaagctgct tcgtcgttca agggtgctcc tttgcctgct     240
cgcagctacg acgtctttgt ttcgaacgcg ggcgtcgctg cgttctcgcc cacagccgac     300
```

```
cacgatgata aggagtggca gaacttgctt gccgtgaact tgtcgtcgcc cattgccctc    360
acgaaggccc tcttgaagga tgtctccgaa aggcctgtgg acaagccact gcagattatc    420
tacatttcgt cggtggccgg cttgcatggc gccgcgcagg tcgccgtgta cagtgcatct    480
aaggccggtc ttgatggttt tatgcgctcc gtcgcccgtg aggtgggccc gaagggcatc    540
catgtgaact ccatcaaccc cggatacacg aagactgaaa tgaccgcggg cattgaagcc    600
cttcctgatt tgcctatcaa ggggtggatc gagcccgagg caattgctga cgcggttctg    660
tttctggcaa agtccaagaa tatcaccggc acaaacattg tggtcgacaa tggcttgatt    720
gcttaa                                                                726
```

```
<210> SEQ ID NO 25
<211> LENGTH: 759
<212> TYPE: DNA
<213> ORGANISM: Candida magnoliae

<400> SEQUENCE: 25
atgtcttatc aaatgtcttc ttctgctcca tcctccacct ccctgaatgc gcttgtcacg     60
ggcggcagcc gcggcattgg cgaagccact gccattaagc tcgccgagga gggctacagc    120
gtcacgattg cgtctcgcgg ccttaagcag ctcgaggctg tgaaggccaa actacccatt    180
gtgaagcagg acaggttca ccacgtgtgg cagcttgatc tcagtgatgt cgacgctgcg     240
gccgccttca agggtcgcc gctacctgcc agccgctacg acgtgctcgt cagcaatgct    300
ggcgtggccc agtttagccc gttcatcgag catgcgaagc aggactggtc gcagatgctt    360
gccatcaatc tggcggcacc cattgcgctg cccagacat tgctaaggc cattggcgac     420
aagccgcgca acaccggc ccacattgtg tttgtctcgt cgaacgtctc gttgcgaggc    480
ttcccgaaca tcgcgtctca cacgccacg aaagccggca ttgacggctt catgcgctcg    540
gtcgcacgcg aactgggggcc cagcggcatt aacgtgaact ccgtgaaccc cggccacg    600
cggacggaga tgacgaaggg cattgacgtc ggcacgatcg atatgccgat caagggctgg    660
atcgagcccg aggcgattgc ggatgccgtg ctcttcgtgg tcaagtcgaa gaacattacg    720
ggcacgaccg ttgttgtcga caacggctcc tccgcttga                           759
```

```
<210> SEQ ID NO 26
<211> LENGTH: 759
<212> TYPE: DNA
<213> ORGANISM: Candida magnoliae

<400> SEQUENCE: 26
atgaccacct cctccaccct ccctccacc tcctcccgct ctctaaacgc tcttgtcacc      60
ggcgctagcc gcggcattgg cgaggccact gcaatcaagc tagcatctga gggatacagc    120
gttacgcttg catctcgtag cctcgagcag ctcaaggctt tgaaggagaa gttgccgtt    180
gtgaagcagg accagacgca ccacgtctgg cagctcgact tgagcgacgt cgacgccgct    240
gccacgttca agggctcccc cttgccggcc agcagctacg acgccgtcat cagcaatgcc    300
ggtgttgctc agttctctcc gttgtcggaa cacgccaggg aggactggtc tcagatgctg    360
acgatcaacc tcgcggctcc cattgccctc gcgcaggcgt tgtgaaggc cattggcgac    420
aagaagcgcg acatcccggc ccaaattgtc tttgtttcgt cgaatgtcgt gatgcgtggc    480
ctcccttacc tcggcatcta cacggcttcg aaggctggta tcgatggctt catgcgctcg    540
gccgcccgcg agctgggacc caagggtatc aacgtgaact cagtaaaccc gggcgccacg    600
cagaccgaga tgacgaaggg cgttgatgtc aacgccctcg acctgccgat caagggatgg    660
```

```
attcagctcg aggctgtcgc ggacgccgtg ctcttcgtgg tccagtcgaa gaacattacc    720
ggcacgacga ttgttgtcga caacggctcc gtcgcttga                           759

<210> SEQ ID NO 27
<211> LENGTH: 723
<212> TYPE: DNA
<213> ORGANISM: Candida magnoliae

<400> SEQUENCE: 27
atgaatgcct tagttactgg tgcgagccgc gggatcggcg aagcaattgc ggtgaagctg     60
gccgaggacg ggtacagcgt gacactggcc tcgcgctctc ttgaaaagct ggagtcgctc    120
aagaaagggc tgccggtcgt gaaggacggc caagcacatc atgtatggga gcttgatctc    180
ggtgatgttg atgccgcgtc atccttcaag ggggcgcctc tgcctgccga ggcctatgac    240
gtgttcgtca gtaacgctgg aatggccaaa tccaccttga tggtagacca tcccattgac    300
gagctgcagg acatgattaa cgtgaatctt gtgtcgccaa ttgcactcac acagggcctt    360
gtcaaggctc tgacagaatc taagcgagac aagcctgcgc atatcgtgtt catgtcgtcc    420
atccgctcgt tcagggcat tccgaatggc gcggtgtaca cgccacaaa gagtggtctt    480 gacggattca tgcgatccat tgcgcgagag ctgggccctc agggcatcca cgtcaactct    540
gtgtgccccg gattcgtgca aacgaaatg acgcgcaagg ttgatatgga gtcgaagaaa    600
gaccagctac ccatcgccgg ctggatccag cccgacgcga ttgctgacac cgttctgttt    660
tttgtgaaat cgaagaacat cacgggccag gcaattgtcg ttgacaatgg catcactgtc    720
tga                                                                  723

<210> SEQ ID NO 28
<211> LENGTH: 735
<212> TYPE: DNA
<213> ORGANISM: Candida gropengiesseri

<400> SEQUENCE: 28
atgccctctg gactcaatgc tcttgtcact ggcggcagcc gcggaatcgg cgctgccgct     60
gctaccaagc tcgccgctgc aggatacaac gtcacggttg cgtcccgcgg ggtcgaggct    120
ctgaataagg tcaaggcctc cttgcctgtt gtcaaggagg ccagcagca ccatgtctgg    180 cagctcgacg taagcgatct cgcagcgtgt tctggcttca agggatctcc gctgccggct    240
aagagctacg atgttgttgt tgttaacgcc ggcgtcgcga acctgagccc gctggctgcc    300
caggacgacg acgtcattca gaacattgtg accgtgaacc tgctgtcgcc gattgcgctg    360
gtgaagtcgc tgatcaaggc gtacggcgag gtcctcgcg cgacaccggc ccacattgtg    420
tttgtgtcgt cggtggccgc gatccgtggg ttccccaacg cgccgtcta tagctcgacg    480 aagagtgcgc tcgacgggct gacgcggtcg ctggcgaagg agctggggcc ccagaacatc    540
cgggtcaact ccgtgaaccc cggcttcacg aggaccgagc tggccagcgg cgtcgacatt    600
gacgccgtga cgcagagctc tccgatcaag gggtggggttg agccggaggc gattggcgat    660
gcgattttgt ttctcgcgac gtcgaaccac atcacgggca cgatcaccgt catcgacaac    720
ggcactagcg cgtag                                                     735

<210> SEQ ID NO 29
<211> LENGTH: 750
<212> TYPE: DNA
<213> ORGANISM: Candida sp.
```

<400> SEQUENCE: 29

```
atgtcctcct cttcctcctc gactcctctc aacgctctcg tcaccggtgc cagccgcggc      60
atcggtgagg tcatctctct ccagctcgcc aacgagggct acaatgttac cctcgcagcc     120
cgcagtcttg acgacctcaa tgcggtgaag gctaagctcc ctatcgtaag ggatgcccag     180
aagcactctg tctggccgct cgacattagc gatatcgacg ccgtgacgaa cttcaaggga     240
tcgcccctgc cggccgagaa gtacgatctg ttcgtcagca acgccggcgt ggtcgacttc     300
gctccgcttg tccaccagag ccccgagagc atcagcagcc tgttcaatgt gaacctaatc     360
gcgcctgttg ccttgacaaa agctcttctt aaggcgttcg gtgacagccc tcgcaagact     420
acgactcact ttatctacgt ttcgtccgtt gttgccctcc gcggcttccc caatgttgcg     480
gtttacagct cctccaagag cggcctcgac gggtttgtgc gctcccttgc cgccgaggtt     540
gctccgctca acatccgcgt caactccatt aacccaggcc ctaccaagac tgagatgacc     600
gcttccctgg atgttgaggc gtttactgcg ggcaacccca tcaagggttg gatttacccc     660
gatgctattg ctgatggagt ggtgtacctg gcgaagtcga gaacattac tggtatcacc      720
ctccaagtcg acaacggcgc cggcatctaa                                      750
```

<210> SEQ ID NO 30
<211> LENGTH: 726
<212> TYPE: DNA
<213> ORGANISM: Candida vaccinii

<400> SEQUENCE: 30

```
atgaggtcga cacctaacgc ccttgtgact ggcggcagcc gcggcattgg cgcggccgct      60
gcaattaaac tcgccgaggc aggctacagc gtgacgctcg cgtcgcgcgg tctcgacaag     120
ctcaacgagg tgaaggccaa gcttcctgtc gtgaagcagg gccaggagca ccatgtatgg     180
cagcttgatc tcagcgacgt gcaggccgcg ctcgagttca agggcgcacc gctgcccgcg     240
agtaagtacg atttgtttgt ctcgaacgcc ggcgtggcta ctttctcgcc aacggctgag     300
catgacgaca aggactggca gaacattatt gccgtgaact tgacatcgcc cattgccatt     360
acgaaggcgc tcgttaaggc cgttggcgag cgctcaaacg ataacccgtt tcagatcgcg     420
ttcctgtcat cggcggccgc cctgcgcggt gtgccgcaga ccgctgttta cagcgctacg     480
aaggccggcc tcgacggctt cacgcgctcg ctcgccaagg agctcggccc aaagggcatc     540
catgtgaaca tcgtacaccc tggatggacg cagaccgaga tgactgcggg tgtagatgag     600
cctagggata cgcccatccc gggctggatc cagccggaag ccatcgccga ggccattgtg     660
tatctcgcga agtcaaagaa catcacggga acgaacatcg ttgtcgacaa cggcctgact     720
atttaa                                                                726
```

<210> SEQ ID NO 31
<211> LENGTH: 12
<212> TYPE: PRT
<213> ORGANISM: artificial sequence
<220> FEATURE:
<223> OTHER INFORMATION: artificial partial amino acid sequence of oxidoreductases

<400> SEQUENCE: 31

Asn Ala Leu Val Thr Gly Ala Ser Arg Gly Ile Gly
1               5                   10

<210> SEQ ID NO 32
<211> LENGTH: 12

```
<212> TYPE: PRT
<213> ORGANISM: artificial sequence
<220> FEATURE:
<223> OTHER INFORMATION: artificial partial amino acid sequence of
      oxidoreductases

<400> SEQUENCE: 32

Asn Ala Leu Val Thr Gly Gly Ser Arg Gly Ile Gly
1               5                   10

<210> SEQ ID NO 33
<211> LENGTH: 5
<212> TYPE: PRT
<213> ORGANISM: artificial sequence
<220> FEATURE:
<223> OTHER INFORMATION: artificial partial amino acid sequence of
      oxidoreductases

<400> SEQUENCE: 33

Gly Tyr Ser Val Thr
1               5

<210> SEQ ID NO 34
<211> LENGTH: 5
<212> TYPE: PRT
<213> ORGANISM: artificial sequence
<220> FEATURE:
<223> OTHER INFORMATION: artificial partial amino acid sequence of
      oxidoreductases

<400> SEQUENCE: 34

Gly Tyr Asn Val Thr
1               5

<210> SEQ ID NO 35
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 35

Gly Tyr Gly Ile Thr Leu
1               5

<210> SEQ ID NO 36
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 36

Val Leu Ala Lys Leu Pro
1               5

<210> SEQ ID NO 37
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 37

Val Lys Ala Lys Leu Pro
```

```
1               5
```

<210> SEQ ID NO 38
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 38

```
Phe Lys Gly Ala Pro Leu Pro Ala
1               5
```

<210> SEQ ID NO 39
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 39

```
Phe Arg Gly Ala Pro Leu Pro Ala
1               5
```

<210> SEQ ID NO 40
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 40

```
Leu Lys Gly Ala Pro Leu Pro Ala
1               5
```

<210> SEQ ID NO 41
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 41

```
Ser Pro Ile Ala Leu Thr Lys
1               5
```

<210> SEQ ID NO 42
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 42

```
Ser Pro Val Ala Leu Thr Lys
1               5
```

<210> SEQ ID NO 43
<211> LENGTH: 7
<212> TYPE: PRT
<213> ORGANISM: artificial sequence
<220> FEATURE:
<223> OTHER INFORMATION: artificial partial amino acid sequence of oxidoreductases

<400> SEQUENCE: 43

Ser Gln Ile Ala Leu Thr Gln
1               5

<210> SEQ ID NO 44
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 44

Ala Val Tyr Ser Ala Ser Lys
1               5

<210> SEQ ID NO 45
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 45

Ala Val Tyr Ser Ala Thr Lys
1               5

<210> SEQ ID NO 46
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 46

Gly Val Tyr Ser Ala Thr Lys
1               5

<210> SEQ ID NO 47
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 47

Pro Ile Lys Gly Trp Ile
1               5

<210> SEQ ID NO 48
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 48

Pro Ile Glu Gly Trp Ile
1               5

<210> SEQ ID NO 49

```
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 49

Pro Ile Gly Gly Trp Ile
1               5

<210> SEQ ID NO 50
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 50

Pro Ile Ser Gly Trp Ile
1               5

<210> SEQ ID NO 51
<211> LENGTH: 5
<212> TYPE: PRT
<213> ORGANISM: artificial sequence
<220> FEATURE:
<223> OTHER INFORMATION: artificial partial amino acid sequence of
      oxidoreductases

<400> SEQUENCE: 51

Gly Tyr Gly Val Thr
1               5

<210> SEQ ID NO 52
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 52

Phe Lys Ala Ala Pro Leu Pro Ala
1               5

<210> SEQ ID NO 53
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 53

Phe Lys Gly Ser Pro Leu Pro Ala
1               5

<210> SEQ ID NO 54
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 54
```

```
Gly Ile Gly Arg Ala Thr
1               5

<210> SEQ ID NO 55
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 55

Gly Ile Gly Arg Ala Ser Ala
1               5

<210> SEQ ID NO 56
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 56

Gly Ile Gly Arg Glu Thr
1               5

<210> SEQ ID NO 57
<211> LENGTH: 6
<212> TYPE: PRT
<213> ORGANISM: artificial sequence
<220> FEATURE:
<223> OTHER INFORMATION: artificial partial amino acid sequence of
      oxidoreductases

<400> SEQUENCE: 57

Asn Asn Ala Gly Ile Gly
1               5

<210> SEQ ID NO 58
<211> LENGTH: 7
<212> TYPE: PRT
<213> ORGANISM: artificial sequence
<220> FEATURE:
<223> OTHER INFORMATION: artificial partial amino acid sequence of
      oxidoreductases

<400> SEQUENCE: 58

Asn Asn Ala Gly Ile Glu Gly
1               5

<210> SEQ ID NO 59
<211> LENGTH: 9
<212> TYPE: PRT
<213> ORGANISM: artificial sequence
<220> FEATURE:
<223> OTHER INFORMATION: artificial partial amino acid sequence of
      oxidoreductases

<400> SEQUENCE: 59

Ile Arg Val Val Ala Ile Ala Pro Gly
1               5

<210> SEQ ID NO 60
<211> LENGTH: 9
<212> TYPE: PRT
<213> ORGANISM: artificial sequence
<220> FEATURE:
```

```
<223> OTHER INFORMATION: artificial partial amino acid sequence of
      oxidoreductases

<400> SEQUENCE: 60

Ile Arg Val Asn Ala Ile Ala Pro Gly
1               5

<210> SEQ ID NO 61
<211> LENGTH: 9
<212> TYPE: PRT
<213> ORGANISM: artificial sequence
<220> FEATURE:
<223> OTHER INFORMATION: artificial partial amino acid sequence of
      oxidoreductases

<400> SEQUENCE: 61

Ile Arg Val Asn Ala Ile Cys Pro Gly
1               5

<210> SEQ ID NO 62
<211> LENGTH: 9
<212> TYPE: PRT
<213> ORGANISM: artificial sequence
<220> FEATURE:
<223> OTHER INFORMATION: artificial partial amino acid sequence of
      oxidoreductases

<400> SEQUENCE: 62

Ile Arg Val Val Gly Ile Ala Pro Gly
1               5

<210> SEQ ID NO 63
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 63

Pro Glu Gln Ile Ala Gly Ala Val
1               5

<210> SEQ ID NO 64
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 64

Pro Glu Ala Ile Ala Asn Ala Val
1               5

<210> SEQ ID NO 65
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 65

Pro Glu Glu Val Ala Asn Ala Val
1               5
```

```
<210> SEQ ID NO 66
<211> LENGTH: 8
<212> TYPE: PRT
<213> ORGANISM: artificial sequence
<220> FEATURE:
<223> OTHER INFORMATION: artificial partial amino acid sequence of
      oxidoreductases

<400> SEQUENCE: 66

Pro Glu Ala Ile Ala Asn Ala Val
1               5

<210> SEQ ID NO 67
<211> LENGTH: 33
<212> TYPE: DNA
<213> ORGANISM: artificial sequence
<220> FEATURE:
<223> OTHER INFORMATION: primer

<400> SEQUENCE: 67
gggaattcca tatgatgctc gaggggaagg tcg                                   33

<210> SEQ ID NO 68
<211> LENGTH: 31
<212> TYPE: DNA
<213> ORGANISM: artificial sequence
<220> FEATURE:
<223> OTHER INFORMATION: primer

<400> SEQUENCE: 68
cacatgcatg cgaatgctcg aggggaaggt c                                    31

<210> SEQ ID NO 69
<211> LENGTH: 34
<212> TYPE: DNA
<213> ORGANISM: artificial sequence
<220> FEATURE:
<223> OTHER INFORMATION: primer

<400> SEQUENCE: 69
cccaagctta ttacttgaac tccgcgtagc cgtc                                 34

<210> SEQ ID NO 70
<211> LENGTH: 750
<212> TYPE: DNA
<213> ORGANISM: artificial sequence
<220> FEATURE:
<223> OTHER INFORMATION: semisynthetic gene sequence from Rubrobacter
      xylanophilus

<400> SEQUENCE: 70
atgctggaag gtaaagtggc agtcatcacc ggtgcaggca gcggcattgg gcgtgccact      60
gcgctgcgtt ttgcgcgtga aggcgctcgc gtcgttgtgg ccgagctgga tgaacgtcgc     120
ggtgaggaag ttgtacgtga gattctggaa tctggcgggg aggccgtctt cgtgaggacg     180
gacgtctcgg agttcgagca ggttgaggcc gccgtcgagc gcgccgtcga ggagtacggg     240
acgctggacg tcatgttcaa caacgccggc atcgggcact acgcccccct gctggagcac     300
gacccggagc actacgaccg ggtggtccgg gtgaaccagt acggcgtcta ctacgggata     360
ctcgccgccg gcaggaagat ggccgagctg gagaaccccg gcgtgatcat caacaccgcc     420
tcggtctacg ctttcctggc ctcccccggt gtgatcggct atcacgcttc caaggggcg      480 gtgaagatga tgacccaggc cgcagccctg gagctcgccc ccacggcat acgggtcgtc     540 gccatcgccc cgggcggggt ggacaccccg atcatccagg gctacaagga catgggcctc     600
```

```
ggtgagcggc tggcccgcgg ccagatgcgt cgcaggctcc agaccccga gcagatcgcc    660 ggcgccgtcg tcctgctcgc caccgaggag gcagacgcca taaacggctc ggtggtgatg    720
accgacgacg gctacgcgga gttcaagtaa                                    750
```

<210> SEQ ID NO 71
<211> LENGTH: 30
<212> TYPE: DNA
<213> ORGANISM: artificial sequence
<220> FEATURE:
<223> OTHER INFORMATION: primer

<400> SEQUENCE: 71

```
cctagctagc atgctggaag gtaaagtggc                                     30
```

<210> SEQ ID NO 72
<211> LENGTH: 22
<212> TYPE: DNA
<213> ORGANISM: artificial sequence
<220> FEATURE:
<223> OTHER INFORMATION: primer

<400> SEQUENCE: 72

```
cctttrcctg chagcagcta yg                                             22
```

<210> SEQ ID NO 73
<211> LENGTH: 23
<212> TYPE: DNA
<213> ORGANISM: artificial sequence
<220> FEATURE:
<223> OTHER INFORMATION: primer

<400> SEQUENCE: 73

```
ggctggatcc agcccttrat sgg                                            23
```

<210> SEQ ID NO 74
<211> LENGTH: 39
<212> TYPE: DNA
<213> ORGANISM: artificial sequence
<220> FEATURE:
<223> OTHER INFORMATION: primer

<400> SEQUENCE: 74

```
ggaattccat atgatgaacg ctctagtgac cggtggtag                           39
```

<210> SEQ ID NO 75
<211> LENGTH: 38
<212> TYPE: DNA
<213> ORGANISM: artificial sequence
<220> FEATURE:
<223> OTHER INFORMATION: primer

<400> SEQUENCE: 75

```
cccaagctta ttaaaccgtg attccgttgt caactgac                            38
```

PROCESS FOR THE ENANTIOSELECTIVE ENZYMATIC REDUCTION OF INTERMEDIATES

The invention relates to a process for the enantioselective enzymatic reduction of a keto compound of general formula I

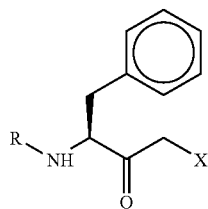

(I)

wherein R may represent any protective group for amino functions (tert. butyloxycarbonyl group, benzyloxycarbonyl group, 9-fluorenylmethoxycarbonyl group) and X=—Cl, —CN, —OH, Br, F,

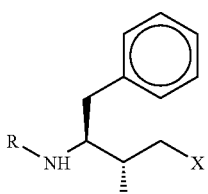

(II)

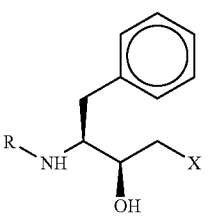

(III)

to the compounds of formulae II (R,S-alcohol) and III (S,S-alcohol), respectively, with an oxidoreductase in the presence of a cofactor.

Preferred compounds of formula I contain the butyloxycarbonyl group or the benzyloxycarbonyl group as an amino protective group and a chlorine atom in place of X.

Chiral alcohols of general formulae II and III are important intermediates in the production of protease inhibitors for the therapy of HIV. Such protease inhibitors are, for example, Ritonavir, Amprenavir, Fosamprenavir, Atazanavir or Darunavir.

Intermediates of formulae II (R,S-alcohol) and III (S,S-alcohol), respectively, are obtainable, for example, by enantioselective reduction of the corresponding keto compounds of formula I, which is performed chemically in current production processes. In doing so, the chemically catalyzed reduction has the disadvantage that, on the one hand, it may result in byproducts due to harsh reaction conditions and, on the other hand, yields unsatisfactory enantiomeric and diastereomeric excesses, respectively, and is technically feasible only with very large efforts. Thereby, the intermediate of formula II (R,S-alcohol) in its enantiomerically enriched form is chemically accessible with more difficulty than that of formula III (S,S-alcohol).

For this reason, there have, for quite some time, been endeavours to develop biocatalytic processes which allow for the enantioselective reduction of said intermediates. Biocatalytic processes usually operate under mild conditions, for which reason they can be expected to enable the reduction of the keto compounds of formula I without the formation of further byproducts. So far, however, it has not been possible to find any suitable biocatalysts by means of which the enzymatic reduction is possible with isolated enzymes.

As far as we know, only few publications exist in which reactions of ketones of formula I with strains of *Rhodococcus* or *Streptomyces* in whole-cell processes are described (Tetrahedron Asymmetry 14 (2003) 3105-3109, Tetrahedron Asymmetry 8 (1997) p. 2547). However, the reactions have thereby occurred only with whole cells and lysates, respectively, of wild strains and have thus been carried out only at very low concentrations far below 2% and without coenzyme regeneration. Enzymatic reduction processes applicable on an industrial scale have not been available so far, and the enzymes involved in the reaction have neither been isolated nor identified.

It is the object of the invention to provide a process which enables the economic production of enantiomerically pure and, respectively, enantiomerically enriched intermediates of general formulae II and III in high yields and with high enantiomeric purity without any byproducts.

According to the invention, said object is achieved by a process of the initially mentioned kind which is characterized in that the oxidoreductase used for the production of the compound of formula II (R,S-alcohol)
  a) comprises an amino acid sequence according to SEQ ID No: 1, SEQ ID No: 2, SEQ ID No: 3 or SEQ ID No: 4,
  b) comprises an amino acid sequence in which at least 60% of the amino acids are identical to those of amino acid sequences SEQ ID No: 1, SEQ ID No: 2 or SEQ ID No: 3, SEQ ID No: 4, or
  c) comprises an amino acid sequence in which at least 70% of the amino acids are identical to those of amino acid sequences SEQ ID No: 1, SEQ ID No: 2 or SEQ ID No: 3, SEQ ID No: 4, or
  d) is encoded by the nucleic acid sequence SEQ ID No: 16, SEQ ID No: 17, SEQ ID No: 18, SEQ ID No: 19, or
  e) is encoded by a nucleic acid sequence which hybridizes to SEQ ID No: 16, SEQ ID No: 17, SEQ ID No: 18, SEQ ID No: 19 under stringent conditions,
  f) has a length of from 220 to 260 amino acids and comprises one or several of the partial sequences selected from the group consisting of sequences SEQ ID No: 31 to SEQ ID No: 51 and reduces the compound of formula I preferably to the compound of formula II.

nalvtgasrgig (SEQ ID No: 31) nalvtggsrgig (SEQ ID No: 32), gysvt (SEQ ID No: 33), gynvt (SEQ ID No: 34), gygitl (SEQ ID No: 35), gygvt (SEQ ID No: 51) vlaklp (SEQ ID No: 36), vkaklp (SEQ ID No: 37)
fkgaplpa (SEQ ID No: 38), frgaplpa (SEQ ID No: 39), lkgaplpa (SEQ ID No: 40), spialtk (SEQ ID No: 41), spvaltk (SEQ ID No: 42), sqialtq (SEQ ID No: 43), avysask (SEQ ID No: 44), avysatk (SEQ ID No: 45), gvysatk (SEQ ID No: 46), pikgwi (SEQ ID No: 47), piegwi (SEQ ID No: 48), piggwi (SEQ ID No: 49) and pisgwi (SEQ ID No: 50), Furthermore, said object is achieved by a process of the initially mentioned kind which is characterized in that the oxidoreductase used for the production of the compound of formula III (S,S-alcohol)
  a) comprises an amino acid sequence according to SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15,
b) comprises an amino acid sequence in which at least 60% of the amino acids are identical to those of amino acid sequences according to SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, or
c) is encoded by the nucleic acid sequence SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID No: 29 or SEQ ID No: 30, or
d) is encoded by a nucleic acid sequence which hybridizes to SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID No: 29 or SEQ ID No: 30 under stringent conditions,
e) has a length of from 220 to 260 amino acids and comprises one or several of the partial sequences selected from the group consisting of sequences SEQ ID No: 31 to SEQ ID No: 66 and reduces the compound of formula I preferably to the compound of formula III.

nalvtgasrgig (SEQ ID No: 31) nalvtggsrgig (SEQ ID No: 32), gysvt (SEQ ID No: 33), gynvt (SEQ ID No: 34), gygitl (SEQ ID No: 35), gygvt (SEQ ID No: 51) vlaklp (SEQ ID No: 36), vkaklp (SEQ ID No: 37)
fkgaplpa (SEQ ID No: 38), frgaplpa (SEQ ID No: 39), lkgaplpa (SEQ ID No: 40), fkaaplpa (SEQ ID No: 52), fkgaplpa (SEQ ID No: 53)
spialtk (SEQ ID No: 41), spvaltk (SEQ ID No: 42), sqialtq (SEQ ID No: 43), avysask (SEQ ID No: 44), avysatk (SEQ ID No: 45), gvysatk (SEQ ID No: 46), pikgwi (SEQ ID No: 47), piegwi (SEQ ID No: 48), piggwi (SEQ ID No: 49) and pisgwi (SEQ ID No: 50),
gigrat (SEQ ID No: 54), gigrasa (SEQ ID No: 55), gigret (SEQ ID No: 56), nnagig (SEQ ID No: 57), nnagieg (SEQ ID No: 58),
irvvaiapg (SEQ ID No: 59), irvnaiapg (SEQ ID No: 60), irvnaicpg (SEQ ID No: 61), irvvgiapg (SEQ ID No: 62),
peqiagav (SEQ ID No: 63), peaianav (SEQ ID No: 64), peevanav (SEQ ID No: 65), peaianav (SEQ ID No: 66)

A polypeptide which reduces the compound of formula I preferably to the compound of formula II is understood to be such a polypeptide in which the maximum enantiomeric excess of the R,S-alcohol achievable under optimum reaction conditions amounts to at least 50%. Optimum reaction conditions are thereby understood to be those reaction conditions of a polypeptide under which a polypeptide yields the highest enantiomeric excess of the R,S-alcohol.

It has been found that the polypeptides comprising amino acid sequences SEQ ID No: 1, SEQ ID No: 2, SEQ ID No: 3 and SEQ ID No: 4 show oxidoreductase activity and can be used for reducing the compound of formula I preferably to the compound of formula II (R,S-compound). The achievable enantiomeric excess of the R,S-alcohol amounts to >50%, preferably to >80% and particularly preferably to >95%. The enantiomeric excess achieved when using SEQ ID NO: 1 can, for example, account for up to >99% of the R,S-compound (formula II).

Similarly, it has been found that the polypeptides comprising amino acid sequences SEQ ID No: 5 to SEQ ID No: 15 show oxidoreductase activity and can be used for reducing the compound of formula I preferably to the compound of formula III (S,S-compound). The achievable enantiomeric excess of the R,S-alcohol amounts to >80%, preferably to >90% and particularly preferably to >95%. The enantiomeric excess achieved when using SEQ ID No: 5, SEQ ID No: 6, SEQ ID No: 9 or SEQ ID No: 12 can account for up to >99% of the R,S-compound (formula II).

A number of the mentioned oxidoreductases such as, e.g., SEQ ID Nos: 1, 3, 4, 5, 6, 7 and 15 have the additional advantage that they are able to regenerate the oxidized cofactor formed during the reduction by reducing a secondary alcohol. Thus, a particular economic advantage of said oxidoreductases is also that no further enzyme has to be used for cofactor regeneration in contrast to prior art methods.

A DNA sequence SEQ ID No: 20, which codes for a polypeptide comprising SEQ ID No: 5, is obtainable, for example, from the genome of the organism *Rubrobacter xylanophilus* DSM 9941.

A DNA sequence SEQ ID No: 21, which codes for a polypeptide comprising SEQ ID No: 6, is obtainable, for example, from the genome of the organism *Geobacillus thermodenitrificans* DSM 465.

A DNA sequence SEQ ID No: 22, which codes for a polypeptide comprising SEQ ID No: 7, is obtainable, for example, from the genome of the organism *Chloroflexus aurantiacus DSM* 635.

A DNA sequence SEQ ID No: 23 or a DNA sequence SEQ ID No: 24, which codes for a polypeptide comprising SEQ ID No: 8 or SEQ ID No: 9, respectively, is obtainable, for example, from the organism *Candida magnoliae* DSMZ 70638.

A DNA sequence SEQ ID No: 26, which codes for a polypeptide comprising SEQ ID No: 11, is obtainable, for example, from the organism *Candida magnoliae* DSMZ 70639.

A DNA sequence SEQ ID No: 16, which codes for a polypeptide comprising SEQ ID No: 1, is obtainable, for example, from the organism *Candida magnoliae* CBS 6396.

Furthermore, the oxidoreductases of SEQ ID No: 2, SEQ ID No: 3, SEQ ID No: 4, SEQ ID No: 12, SEQ ID No: 13, SEQ ID No: 14 and SEQ ID No: 15 are obtainable, for example, by homology screening from the strains *Candida magnoliae* CBS 5659, CBS 7318, CBS 2798, JCM 9448, *Candida geochares* MUCL 29832, *Candida* spec. MUCL 40660, *Candida gropengiesseri* MUCL 29836.

Thus, the present invention relates to a process for the reduction of keto compounds of general formula I to compounds of general formulae II and III, respectively, characterized in that one of the compounds II or III is formed clearly in excess, using a polypeptide comprising one of the amino acid sequences SEQ ID No: 1 to SEQ ID No: 15, or a polypeptide which comprises an amino acid sequence which is identical by at least 50% to one of the amino acid sequences SEQ ID No: 1 to SEQ ID No: 15, i.e., a polypeptide which can be derived from the sequences SEQ ID No: 1 to SEQ ID No: 15 by substitution, insertion, deletion or addition of at least one amino acid, or using a polypeptide which is encoded by one of the nucleic acid sequences SEQ ID No: 16 to SEQ ID No: 30 or by nucleic acid sequences which hybridize under stringent conditions to one of the sequences SEQ ID No: 16 to SEQ ID No: 30.

A nucleic acid sequence which hybridizes, for example, to SEQ ID No: 16 under stringent conditions is understood to be a polynucleotide which can be identified via the colony hybridization method, the plaque hybridization method, the Southern hybridization method or comparable methods, using SEQ ID No: 16 as a DNA probe.

For this purpose, the polynucleotide immobilized on a filter is hybridized, for example, to SEQ ID No: 16 in a 0.7-1 M NaCl solution at 60° C. Hybridization is carried out as described, for instance, in Molecular Cloning, A Laboratory Manual, Second Edition (Cold Spring Harbor Laboratory Press, 1989) or in similar publications. Subsequently, the filter is washed with a 0.1 to 2-fold SSC solution at 65° C., wherein a 1-fold SSC solution is understood to be a mixture consisting of 150 mM NaCl and 15 mM sodium citrate.

Furthermore, the present invention relates to polypeptides of amino acid sequences SEQ ID No: 1, SEQ ID No: 2, SEQ ID No: 3, SEQ ID No: 4, SEQ ID No: 11, SEQ ID No: 12, SEQ ID No: 13, SEQ ID No: 14 and SEQ ID No: 15 as well as to polypeptides which are identical by at least 55%, preferably by 65% to 75%, particularly preferably by more than 75%, to one of the amino acid sequences SEQ ID No: 1, SEQ ID No: 2, SEQ ID No: 3, SEQ ID No: 4, SEQ ID No: 11, SEQ ID No: 12, SEQ ID No: 13, SEQ ID No: 14 and SEQ ID No: 15, i.e., to polypeptides which can be derived from the sequences SEQ ID No: 1, SEQ ID No: 2, SEQ ID No: 3, SEQ ID No: 4, SEQ ID No: 11, SEQ ID No: 12, SEQ ID No: 13, SEQ ID No: 14 and SEQ ID No: 15 by substitution, insertion, deletion or addition of at least one amino acid. Furthermore, the invention relates to polypeptides which are encoded by the nucleic acid sequences SEQ ID No: 16, SEQ ID No: 17, SEQ ID No: 18, SEQ ID No: 19, SEQ ID No: 26, SEQ ID No: 27, SEQ ID No: 28, SEQ ID No: 29 or SEQ ID No: 30 or by nucleic acid sequences which hybridize under stringent conditions to one of the sequences SEQ ID No: 16, SEQ ID No: 17, SEQ ID No: 18, SEQ ID No: 19, SEQ ID No: 26, SEQ ID No: 27, SEQ ID No: 28, SEQ ID No: 29 or SEQ ID No: 30.

In the process according to the invention, polypeptides comprising the sequences SEQ ID No: 1 to SEQ ID No: 15 and polypeptides derivable from said polypeptides, respectively, can be used either in a completely purified state, in a partially purified state or as cells containing one of the polypeptides SEQ ID No: 1 to SEQ ID No: 15. The cells used can thereby be provided in a native, permeabilized or lysed state. Preferably, polypeptides comprising the sequences SEQ ID No: 1 to SEQ ID No: 15 and derivatives derivable therefrom, respectively, are overexpressed in a suitable host organism such as, for example, *Escherichia coli*, and the recombinant polypeptide is used for reducing the hydroxy ketone of general formula I.

The enzymatic reduction according to the invention proceeds under mild conditions so that the degradation of the unstable compounds of formula I and thus the formation of undesired byproducts can be largely avoided. The process according to the invention has an enantiomeric purity of the compound of formula II (R,S-compound) of up to 99%, at least, however, of 50% of the R,S-compound, depending on the polypeptide used.

For the compound of formula III (S,S-compound), the process according to the invention has an enantiomeric purity of the compound of formula III (S,S-compound) of up to 99%, at least, however, of 80% of the R,S-compound, depending on the polypeptide used.

A preferred embodiment of the invention is characterized in that the cofactor used in the process is continuously reduced with a cosubstrate. Preferably, NAD(P)H is used as the cofactor, with the NAD(P) formed in the reduction being reduced back to NAD(P)H by means of a cosubstrate.

In the processes according to the invention, the oxidized cofactor NAD or NADP formed by the oxidoreductase/dehydrogenase is preferably regenerated continuously.

According to a preferred embodiment of all processes according to the invention, the oxidized cofactor NAD or NADP is regenerated by oxidation of an alcohol.

Secondary alcohols such as 2-propanol, 2-butanol, 2-pentanol, 3-pentanol, 4-methyl-2-pentanol, 2-heptanol, 2-octanol or cyclohexanol are preferably used as cosubstrates. According to a particularly preferred embodiment, 2-propanol or 4-methyl-2-pentanol is used for coenzyme regeneration. The amount of cosubstrate for the regeneration can range from 5 to 95% by volume, based on the total volume.

Preferably, a secondary alcohol of general formula $R_X R_Y$CHOH is used for cofactor regeneration, wherein $R_X$ and $R_Y$ independently are hydrogen, a branched or unbranched $C_1$-$C_8$-alkyl group and $C_{total} \geq 3$.

According to a further preferred embodiment of the processes according to the invention, an additional oxidoreductase/dehydrogenase is added for the regeneration of the cofactor.

In a further preferred embodiment, a further alcohol dehydrogenase can, in addition, be added for the regeneration of the cofactor. Suitable NADH-dependent alcohol dehydrogenases are obtainable, for example, from baker's yeast, from *Candida parapsilosis* (CPCR) (U.S. Pat. No. 5,523,223 and U.S. Pat. No. 5,763,236, Enzyme Microb. Technol., 1993, 15(11):950-8), *Pichia capsulata* (DE 10327454.4), from *Rhodococcus erythropolis* (RECR) (U.S. Pat. No. 5,523,223), *Norcardia fusca* (Biosci. Biotechnol. Biochem., 63(10), 1999, p. 1721-1729; Appl. Microbiol. Biotechnol., 2003, 62(4):380-6; Epub 2003, Apr. 26) or from *Rhodococcus ruber* (J. Org. Chem., 2003, 68(2):402-6). Suitable cosubstrates for those alcohol dehydrogenases are, for example, the already mentioned secondary alcohols such as 2-propanol (isopropanol), 2-butanol, 2-pentanol, 4-methyl-2-pentanol, 2-octanol or cyclohexanol.

Suitable secondary alcohol dehydrogenases for the regeneration of NADPH are, for example, those as described above and isolated from organisms of the order of Lactobacillales, e.g., *Lactobacillus kefir* (U.S. Pat. No. 5,200,335), *Lactobacillus brevis* (DE 19610984 A1; Acta Crystallogr. D. Biol. Crystallogr. 2000 December; 56 Pt 12:1696-8), *Lactobacillus minor* (DE 10119274), *Leuconostoc carnosum* (A 1261/2005, Kl. C12N) or, as described, those from *Thermoanerobium brockii*, *Thermoanerobium ethanolicus* or *Clostridium beijerinckii*.

However, other enzymatic systems can, in principle, also be used for cofactor regeneration. For example, cofactor regeneration can be effected using NAD- or NADP-dependent formate dehydrogenase (Tishkov et al., J. Biotechnol. Bioeng. [1999] 64, 187-193, Pilot-scale production and isolation of recombinant NAD and NADP specific formate dehydrogenase). Suitable cosubstrates of formate dehydrogenase are, for example, salts of formic acid such as ammonium formate, sodium formate or calcium formate.

In the processes according to the invention, the compound of general formula I is used in the reaction batch preferably in an amount of from 10 g/l to 500 g/l, preferably from 25 g/l to 300 g/l, particularly preferably from 50 g/l to 200 g/l, based on the total volume.

The aqueous portion of the reaction mixture in which the enzymatic reduction proceeds preferably contains a buffer, e.g., a potassium phosphate, tris/HCl or triethanolamine buffer, having a pH value of from 5 to 10, preferably a pH of from 6 to 9. In addition, the buffer can contain ions for stabilizing or activating the enzymes such as, for example, zinc ions or magnesium ions.

While carrying out the process according to the invention, the temperature suitably ranges from about 10° C. to 70° C., preferably from 20° C. to 45° C.

In a further preferred embodiment of the process according to the invention, the enzymatic reaction is carried out in the presence of an organic solvent which is not miscible with water or is miscible with water only to a limited degree. Said solvent is, for example, a symmetric or unsymmetric di($C_1$-$C_6$)alkyl ether, a linear-chain or branched alkane or cycloalkane or a water-insoluble secondary alcohol which, at the same time, represents the cosubstrate. The preferred organic solvents are diethyl ether, tertiary butyl methyl ether, diisopropyl ether, dibutyl ether, butyl acetate, heptane, hexane, 2-octanol, 2-heptanol, 4-methyl-2-pentanol and cyclohexanol. In this case, the solvent can simultaneously also serve as a cosubstrate for cofactor regeneration.

If water-insoluble solvents and cosubstrates, respectively, are used, the reaction batch consists of an aqueous phase and an organic phase. According to its solubility, the compound of the formula is distributed between the organic phase and the aqueous phase. In general, the organic phase has a proportion of from 5 to 95%, preferably from 10 to 90%, based on the total reaction volume. The two liquid phases are preferably mixed mechanically so that, between them, a large surface area is generated. Also in this embodiment, e.g., the NAD(P) formed during the enzymatic reduction can be reduced back to NAD(P)H with a cosubstrate, such as described above.

The concentration of the cofactor, in particular of NADH or NADPH, respectively, in the aqueous phase generally ranges from 0.001 mM to 10 mM, in particular from 0.01 mM to 1 mM.

The TTN (total turn over number=mol of reduced compound of formula I/mol of cofactor used) achieved in the processes according to the invention normally ranges from $10^2$ to $10^5$, preferably, however, it is $\geq 10^3$.

In the process according to the invention, a stabilizer of oxidoreductase/dehydrogenase can also be used. Suitable stabilizers are, for example, glycerol, sorbitol, 1,4-DL-dithiothreitol (DTT) or dimethyl sulfoxide (DMSO).

The process according to the invention is carried out, for example, in a closed reaction vessel made of glass or metal. For this purpose, the components are transferred individually into the reaction vessel and stirred under an atmosphere of, e.g., nitrogen or air.

According to another possible embodiment of the invention, the oxidized cosubstrate (e.g. acetone) can be removed continuously and/or the cosubstrate (e.g. 2-propanol) can be newly added in a continuous manner in order to shift the reaction equilibrium towards the reaction product.

In a further embodiment, the addition of the oxidoreductases according to SEQ ID No: 1 to SEQ ID No: 15 and/or of the cosubstrate may also occur little by little in the course of the process.

After completion of the reduction, the reaction mixture is processed. For this purpose, e.g., the aqueous phase is optionally separated from the organic phase and the organic phase containing the product is filtered. Optionally, the aqueous phase can also be extracted and processed further like the organic phase. Thereupon, the solvent is evaporated from the organic phase and the product of general formula II or III is obtained as a crude product. The crude product can then be purified further or used directly for the synthesis of a resultant product.

In the following, the invention is illustrated further by way of examples.

EXAMPLE 1

Cloning and Providing an Oxidoreductase from *Rubrobacter xylanophilus* DSM 9941 (SEQ ID No: 5)

A) Cultivation of *Rubrobacter xylanophilus* DSM 9941

Cells of *Rubrobacter xylanophilus* DSM 9941 were cultivated in the following medium at 50° C. (pH 7.2) and 140 rpm in a bacteria-shaker: 0.1% yeast extract, 0.1% tryptone, 0.004% $CaSO_4 \times 2\, H_2O$, 0.02% $MgCl_2 \times 6\, H_2O$, 0.01% nitrilotriacetic acid, 100 ml phosphate buffer [5.44 g/l $KH_2PO_4$, 43 g/l $Na_2HPO_4 \times 12\, H_2O$], 500 µl/l 0.01 M Fe citrate, 500 µl/l trace element [500 µl/l $H_2SO_4$, 2.28 g/l $MnSO_4 \times H_2O$, 500 mg/l $ZnSO_4 \times 7\, H_2O$, 500 mg $H_3BO_3$, 25 mg/l $CuSO_4 \times 5\, H_2O$, 25 mg/l $Na_2MoO_4 \times 2\, H_2O$, 45 mg/l $CoCl_2 \times 6\, H_2O$]. On day 6 of the cultivation, cells were separated from the culture medium by centrifugation and stored at −80° C.

B) Amplification of the Gene Coding for Selective Oxidoreductase

Genomic DNA was extracted according to the method described in "Molecular Cloning" by Manniatis & Sambrook. The resulting nucleic acid served as a template for the polymerase chain reaction (PCR) involving specific primers which were derived from the gene sequence published under number 46106817 in the NCBI database. In doing so, the primers were provided in a 5'-terminal position with restriction sites for the endonucleases Nde I and Hind III or Sph I, respectively (SEQ ID No: 67, SEQ ID No: 68, SEQ ID No: 69), for subsequent cloning into an expression vector.

Amplification was carried out in a PCR buffer [10 mM Tris-HCl, (pH 8.0); 50 mM KCl; 10 mM $MgSO_4$; 1 mM dNTP Mix; in each case 20 pMol of primer and 2.5 U of Platinum Pfx DNA Polymerase (Invitrogen)] with 500 ng of genomic DNA and the following temperature cycles:

Cycle 1: 94° C., 2 min
Cycle 2×30: 94° C., 15 sec
54° C., 30 sec
68° C., 60 sec
Cycle 3: 68° C., 7 min
4° C., ∞

The resulting PCR product having a size of about 750 by was restricted after purification over a 1% agarose gel with the aid of the endonucleases Nde I and Hind III or Sph I and Hind III, respectively, and was ligated into the backbone of the pET21a vector (Novagen) or of the pQE70 vector (Qiagen), respectively, which backbone had been treated with the same endonucleases. After transforming 2 µl of the ligation batch into *E. coli* Top 10 F' cells (Invitrogen), plasmid DNA of ampicillin-resistant colonies was tested for the presence of an insert having a size of 750 by means of a restriction analysis with the endonucleases Nde I and Hind III or Sph I and Hind III, respectively. Plasmid preparations from the clones which were positive for the fragment were subjected to a sequence analysis and subsequently transformed into *Escherichia coli* BL21 Star (Invitrogen) and *E. coli* RB791 (genetic stock, Yale), respectively.

C.) Efficient Expression of Polypeptide SEQ ID No: 5 in *Escherichia coli* Cells For an efficient expression of the polypeptide SEQ ID No: 5 in *Escherichia coli* cells, coding DNA SEQ ID No: 70 was used as a template in a PCR reaction for cloning into an expression vector. In the region of the first, this DNA sequence differed in 153 bases from the previously known DNA sequence (SEQ ID No: 20). This modification was conservative and did not result in a change in the amino acid sequence.

Amplification was carried out in a PCR buffer [10 mM Tris-HCl, (pH 8.0); 50 mM KCl; 10 mM $MgSO_4$; 1 mM dNTP Mix; in each case 20 pMol of primer (SEQ ID No: 71, SEQ ID No: 68) and 2.5 U of Platinum Pfx DNA Polymerase (Invitrogen)] with 50 ng of DNA SEQ ID No: 70 as a template and the following temperature cycles:

Cycle 1: 94° C., 2 min
Cycle 2×30: 94° C., 40 sec
56° C., 30 sec
68° C., 60 sec
Cycle 3: 68° C., 7 min
4° C., ∞

The resulting PCR product having a size of about 750 by was ligated after purification over a 1% agarose gel with the aid of the endonucleases Nhe I and Hind III into the backbone of the pET21a vector (Novagen), which backbone had been treated with the same endonucleases. After transforming 2 µl of the ligation batch into *E. coli* Top 10 F' cells (Invitrogen), plasmid DNA of ampicillin-resistant colonies was tested for the presence of an insert having a size of 750 by means of a restriction analysis with the endonucleases Nhe I and Hind III. Plasmid preparations from the clones which were positive for the fragment were subjected to a sequence analysis and subsequently transformed into *Escherichia coli* BL21 Star (Invitrogen).

D.) Preparation of Oxidoreductase from *Rubrobacter xylanophilus* DSM 9941

The *Escherichia coli* strains BL21 Star (Invitrogen, Karlsruhe, Germany) and RB791 (*E. coli* genetic stock, Yale, USA), respectively, which had been transformed with the expression construct, were cultivated in a medium (1% tryptone, 0.5% yeast extract, 1% NaCl) with ampicillin (50 µg/ml) until an optical density of 0.5, measured at 550 nm, was reached. The expression of recombinant protein was induced by adding isopropylthiogalactoside (IPTG) at a concentration of 0.1 mM. 16 hours after the induction at 25° C. and 220 rpm, the cells were harvested and frozen at −20° C.

For enzyme recovery, 30 g of cells were suspended in 150 ml triethanolamine buffer (100 mM, pH=7, 2 mM $MgCl_{2z}$, 10% glycerol) and broken down using a high-pressure homogenizer. Subsequently, the enzyme solution was mixed with 150 ml glycerol and stored at −20° C.

The enzyme solution thus obtained was used for the reduction of compound I (example 3).

In analogy to the procedure mentioned in example 2, the oxidoreductases SEQ ID No: 6 and SEQ ID No: 7 can also be provided.

EXAMPLE 2

Cloning and Providing an Oxidoreductase from *Candida magnoliae* by Molecular Screening (SEQ ID No: 1)

A) Molecular Screening for an Oxidoreductase

Genomic DNA isolated from the cells of *Candida magnoliae* CBS 6396 was used as a template for molecular screening via PCR. In doing so, amplification was carried out in a PCR buffer [16 mM $(NH_4)_2SO_4$; 67 mM Tris-HCl pH 8.3 (at 25° C.); 1.5 m $MgCl_2$; 0.01% Tween 20; 0.2 mM dNTP Mix; in each case 30 pMol of primer (SEQ ID No: 72, SEQ ID No: 73) and 1.25 U of Bio Therm Star Polymerase (Genecraft)] with 50 ng of genomic DNA isolated from the cells of *Candida magnoliae* CBS 6396 as a template and with the following cycles:

Cycle 1: 95° C., 7 min
Cycle 2×28: 94° C., 40 sec
    Temperature drop start 63° C. −0.5° C./step, 30 sec
    68° C., 60 sec
    ×20: 94° C., 40 sec
    53° C., 40 sec
    70° C., 60 sec
Cycle 3: 70° C., 7 min
    4° C., ∞

After the fractionation of the entire PCR batch in the 1% agarose gel, a band of about 400 by was identified and cloned via overhanging adenosine moieties into a Topo-TA vector (Invitrogen) for the determination of the DNA sequence.

The DNA band resulting from the screening reaction exhibited an open reading frame corresponding to the fragment of an oxidoreductase of 137 amino acid residues.

B) Isolation (Total and mRNA)

600 mg of fresh cells were resuspended in 2.5 ml of ice-cold LETS buffer. 5 ml (about 20 g) of glass beads washed in nitric acid and equilibrated with 3 ml phenol (pH 7.0) were added to said cell suspension. The entire batch was then alternately treated by 30 sec of vortexing and 30 sec of cooling on ice, in total for 10 min. Subsequently, 5 ml of ice-cold LETS buffer was added, and this was again vigorously vortexed. Said cell suspension was centrifuged at 4° C. and with 11000 g for 5 min. The aqueous phase was recovered and extracted twice with an equal volume of phenol:chloroform: isoamyl alcohol (24:24:1). This was subsequently followed by the extraction with chloroform. After the final extraction, the total RNA was precipitated at −20° C. for 4 h by adding 1/10 vol. of 5 M $LiCl_2$.

1 mg of total RNA thus obtained was used via Oligo-dT cellulose (NEB Biolabs) for the enrichment of the mRNA molecules.

The determination of the entire sequence coding for the oxidoreductase was accomplished by a RACE (rapid amplification of cDNA ends) according to the method described in "Molecular Cloning" by Manniatis & Sambrook.

The gene sequence coding for the oxidoreductase included 720 base pairs and was equivalent to a length of 239 amino acid residues.

C) Synthesis of a Full-Length Transcript Coding for a Short-Chain ADH from *Candida magnoliae* CBS 6396 by PCR Specific primers were constructed for subsequent cloning of the full-length transcript into the appropriate expression systems. In doing so, a 5'-primer with a recognition sequence for Nde I and a 3'-primer with a recognition sequence for Hind III were modified (SEQ ID No: 74, SEQ ID No: 75). Genomic DNA isolated from the cells of *Candida magnoliae* CBS 6396 served as a template for the polymerase chain reaction. Amplification was carried out in a PCR buffer [10 mM Tris-HCl (pH 8.0); 50 mM KCl; 10 mM $MgSO_4$; 1 mM dNTP Mix; in each case 20 pMol of primer and 2.5 U of Platinum Pfx DNA Polymerase (Invitrogen)] with 50 ng of template and the following temperature cycles:

Cycle 1: 94° C., 2 min
Cycle 2×30: 94° C., 15 sec
    58° C., 30 sec
    68° C., 75 sec
Cycle 3: 68° C., 7 min
    4° C., ∞

The resulting PCR product was restricted after purification over a 1% agarose gel with the aid of the endonucleases Nde I and Hind III and was ligated into the backbone of the pET21a vector (Novagen), which backbone had been treated with the same endonucleases. After transforming 2 µl of the ligation batch into *E. coli* Top 10 F' cells (Invitrogen), plasmid DNAs of ampicillin- (or kanamycin) resistant colonies were tested for the presence of an insert having a size of 750 by means of a restriction analysis with the endonucleases Nde I and Hind. The expression constructs pET21-MIX were sequenced. The gene from *Candida magnoliae* coding for a short-chain oxidoreductase had an open reading frame of a total of 720 by (SEQ ID No: 16), which corresponded to a protein of 239 amino acids (SEQ ID No: 1).

D) Expression of Recombinant Oxidoreductase in *E. Coli* Cells

Competent *Escherichia coli* StarBL21(De3) cells (Invitrogen) and RB791 cells (*E. coli* genetic stock, Yale, USA), respectively, were transformed with the expression constructs pET21-MIX coding for the oxidoreductase. The *Escherichia coli* colonies transformed with the expression constructs were then cultivated in 200 ml of LB medium (1% tryptone, 0.5% yeast extract, 1% NaCl) with 50 µg/ml of ampicillin or 40 µg/ml of kanamycin, respectively, until an optical density of 0.5, measured at 550 nm, was reached. The expression of recombinant protein was induced by adding isopropylthiogalactoside (IPTG) with a concentration of 0.1 mM. After 16 hours of induction at 25° C. and 220 rpm, the cells were harvested and frozen at −20° C. For the activity test, 10 mg of cells were mixed with 500 µl of 100 mM TEA buffer pH 7.0, 1 mM MgCl$_2$ and 500 µl glass beads and digested for 10 min using a globe mill. The lysate obtained was then used in a diluted state for the respective measurements.

The activity test was made up as follows: 960 µl of 100 mM TEA buffer pH 7.0, 1 mM MgCl$_2$, 160 µg NADPH, 10 µl of diluted cell lysate. The reaction was started by adding 10 µl of a 100 mM substrate solution to the reaction mixture.

For enzyme recovery in large amounts, 30 g of cells were resuspended in 150 ml of triethanolamine buffer (100 mM, pH 7, 2 mM MgCl$_2$, 10% glycerol) and digested using a high-pressure homogenizer. Subsequently, the enzyme solution was mixed with 150 ml glycerol and stored at −20° C.

In analogy to the procedure mentioned in example 2, the oxidoreductases SEQ ID Nos: 2, 3, 4, 8, 9, 10, 11, 12, 13, 14, 15 can also be provided.

EXAMPLE 3

Characterization of Oxidoreductases SEQ ID No: 1 to SEQ ID No: 15 with Regard to their Reduction Properties of the Compound of Formula I The oxidoreductases of sequences SEQ ID No: 1 to SEQ ID No: 15 were examined as follows for the conversion of the compound of formula I.

Reaction Batch A (without Coenzyme Regeneration)

| | |
|---|---|
| 160 µl | buffer (triethanolamine 100 mM pH = 7, 1 mM MgCl$_2$, 10% glycerol) |
| 150 µl | NAD(P)H (40 mg/ml) = 6 mg |
| 20 µl | 2-propanol |
| 2 mg | compound of formula I |
| 50 µl | enzyme solution according to example 1D |

Reaction Batch B (with Coenzyme Regeneration)

| | |
|---|---|
| 400 µl | buffer (triethanolamine 100 mM pH = 7, 1 mM MgCl$_2$, 10% glycerol) |
| 0.05 mg | NAD(P)H |
| 50 µl | 2-propanol |
| 10 mg | compound of formula I |
| 50 µl | enzyme solution according to example 1D |

After 24 h of incubating samples A and B, 1 ml of acetonitrile was in each case added to the complete reaction batches, the reaction batch was centrifuged off and transferred into a HPLC analysis vessel (1 mg/ml).

The reaction batches were analyzed via HPLC (Nucleodur 100 5 C18 ec, 125 mm, diameter 4 mm, Macherey-Nagel). A flow of 1 ml/min and a solvent system of acetonitrile (B) and water (A) were used. The compounds of formulae I, II and III could be separated within 10 min with an increasing linear gradient from 40% to 80% of acetonitrile.

The retention times were (ketone formula I) 10.0 min; (R,S-compound formula II) 9.3 min and (S,S-compound formula III) 8.5 min.

Results

| | batch A | | batch B | |
|---|---|---|---|---|
| | conversion (% of reduced ketone) | enantio-selectivity (enantiomer [ee] | conversion (% of reduced ketone) | enantio-selectivity (enantiomer [ee] |
| SEQ ID No 1 | 38% | R, S (99%) | 38% | R, S (99%) |
| SEQ ID No 2 | 39% | R, S (80%) | 55% | R, S (82%) |
| SEQ ID No 3 | 100% | R, S (50%) | 100% | R, S (50%) |
| SEQ ID No 4 | 50% | R, S (60%) | 50% | R, S (60%) |
| SEQ ID No 5 | 75% | S, S (>99%) | 20% | S, S (>99%) |
| SEQ ID No 6 | 85% | S, S (>98%) | 40% | S, S (>98%) |
| SEQ ID No 7 | 90% | S, S (>90%) | 80% | S, S (>90%) |
| SEQ ID No 8 | 80% | S, S (80%) | 50% | S, S (80%) |
| SEQ ID No 9 | 100% | S, S (>99%) | 90% | S, S (>99%) |
| SEQ ID No 10 | 90% | S, S (>80%) | 90% | S, S (>80%) |
| SEQ ID No 11 | 95% | S, S (96%) | 95% | S, S (96%) |
| SEQ ID No 12 | 60% | S, S (>98%) | 30% | S, S (>98%) |
| SEQ ID No 13 | 50% | S, S (90%) | 80% | S, S (90%) |
| SEQ ID No 14 | 100% | S, S (80%) | 100% | S, S (70%) |
| SEQ ID No 15 | 34% | S, S (70%) | 40% | S, S (70%) |

EXAMPLE 4

Conversion of the Compound of Formula I to the Compound of Formula II (R,S-Compound) Via Oxidoreductase SEQ ID No: 1

For the conversion of the compound of formula I to the compound of formula II (R,S-compound), 2.25 ml of an enzyme suspension of SEQ ID No: 1 (see example 1D) and 75 units (=2 ml) of the overexpressed alcohol dehydrogenase from *Thermoanerobium brockii* were in each case added to a mixture of 3 ml of a buffer (100 mM TEA, pH=8, 10% glycerol), 1.5 g of the compound of formula I, 0.3 mg NADP and 7 ml 4-methyl-2-pentanol.

The reaction mixture was incubated at room temperature under constant thorough mixing. After 48 h, more than 95% of the compound of formula I used had been reduced to the compound of formula II. The enantiomeric excess amounted to >98%.

EXAMPLE 5

Conversion of the Compound of Formula I to the Compound of Formula III (S,S-Compound) Via Oxidoreductase SEQ ID No: 5

For a further conversion of the compound of formula I to the compound of formula III (S,S-compound), a mixture of 600 µl of a buffer (100 mM TEA, pH=9), 200 µl 2-propanol, 50 mg of the compound of formula I, 0.1 mg NAD and 200 µl of enzyme suspension SEQ ID No: 5 (see example 1 D) was incubated in an Eppendorf reaction vessel. The reaction mixture was incubated at room temperature under constant thorough mixing. After 48 h, more than 90% of the compound of formula I used had been reduced to the compound of formula III (S,S). The enantiomeric excess amounted to >98%.

The invention claimed is:

1. A process for the enantioselective enzymatic reduction of a keto compound of general formula I:

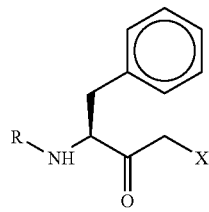

(I)

wherein R is any protective group for amino functions and X=Cl, CN, OH, Br, or F, to the hydroxy compound of general formula II (R,S-compound):

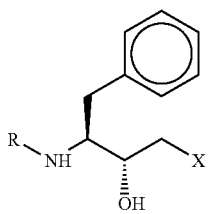

(II)

wherein R and X have the same meaning as in formula I, with the keto compound being reduced with an isolated oxidoreductase in the presence of a cofactor NADH or NADPH, wherein the oxidoreductase a) comprises an amino acid sequence according to SEQ ID No: 1, or
b) is a polypeptide having greater than 75% amino acid sequence identity to SEQ ID No: 1 and enantiomeric selectivity of greater than 80% toward the hydroxyl compound of general formula II, or
c) is encoded by the nucleic acid sequence SEQ ID NO:16, or
d) is encoded by a nucleic acid sequence which hybridizes to a full length sequence of SEQ ID NO:16 when hybridization is carried out in a 0.7-1 M NaCl solution at 60° C. and washing is carried out with a 0.1 to 0.5-fold SSC solution at 65° C. and enantiomeric selectivity of at least 80% toward the hydroxyl compound of general formula II.

2. A process for the enantioselective enzymatic reduction of a keto compound of general formula I:

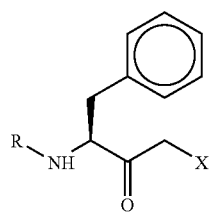

(I)

wherein R is any protective group for amino functions and X=Cl, CN, OH, Br, or F, to the hydroxy compound of general formula II (R,S-compound)

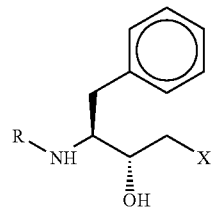

(II)

wherein R and X have the same meaning as in formula I, with the keto compound being reduced with an isolated oxidoreductase in the presence of a cofactor NADH or NADPH, wherein the oxidoreductase a) has an amino acid sequence according to SEQ ID No: 1, or
b) is a polypeptide having greater than 75% amino acid sequence identity to SEQ ID No: 1 and enantiomeric selectivity of at least 80% toward the hydroxyl compound of general formula II, or
c) is encoded by the nucleic acid sequence SEQ ID No: 16, or
d) is encoded by a nucleic acid sequence which hybridizes to a full length sequence of SEQ ID No:16 when hybridization is carried out in a 0.7-1 M NaCl solution at 60° C. and washing is carried out with a 0.1 to 0.5-fold SSC solution at 65° C. and enantiomeric selectivity of at least 80% toward the hydroxyl compound of general formula II.

3. The process according to claim 2, wherein the oxidized cofactor NAD or NADP formed is continuously regenerated by the oxidoreductase.

4. The process according to claim 2, wherein the oxidized cofactor NAD or NADP formed is continuously regenerated by the oxidoreductase through oxidation of a secondary alcohol of general formula $R_X R_Y CHOH$, wherein $R_X$, $R_Y$ independently represent hydrogen, a branched or unbranched C1-C8-alkyl group and $C_{total} \geq 3$.

5. The process according to claim 2, wherein 2-propanol, 2-butanol, 2-pentanol, 4-methyl-2-pentanol, 2-heptanol or 2-octanol is used as a cosubstrate or secondary alcohol, respectively.

6. The process according to claim 2, wherein an additional oxidoreductase/dehydrogenase is added for the regeneration of the cofactor.

7. The process according to claim 2, wherein the compound of formula 1 is present in the reaction batch at a concentration of $\geq 20$ g/l.

8. The process according to claim 2, wherein the TTN (total turn over number=mol of reduced compound of formula I/mol of cofactor used) is $\geq 10^3$.

9. The process according to claim 2, wherein the process is carried out in an aqueous organic two-phase system.

10. The process according to claim 2, wherein, in addition, an organic solvent is used.

11. The process according to claim 2, wherein the specific compound of formula IV is used as the keto compound

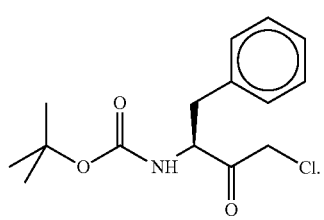

(IV)

12. The process according to claim 1, wherein the oxidized cofactor NAD or NADP formed is continuously regenerated by the oxidoreductase.

13. The process according to claim 1, wherein the oxidized cofactor NAD or NADP formed is continuously regenerated by the oxidoreductase through oxidation of a secondary alcohol of general formula $R_XR_YCHOH$, wherein $R_X$, $R_Y$ independently represent hydrogen, a branched or unbranched C1-C8-alkyl group and $C_{total} \geq 3$.

14. The process according to claim 1, wherein 2-propanol, 2-butanol, 2-pentanol, 4-methyl-2-pentanol, 2-heptanol or 2-octanol is used as a cosubstrate or secondary alcohol, respectively.

15. The process according to claim 1, wherein an additional oxidoreductase/dehydrogenase is added for the regeneration of the cofactor.

16. A process according to claim 2, wherein the compound of formula I is present in the reaction batch at a concentration of $\geq 50$ g/l.

17. A process according to claim 2, wherein the compound of formula I is present in the reaction batch at a concentration of $\geq 100$ g/l.

18. An isolated oxidoreductase adapted for the enantioselective enzymatic reduction in the presence of a cofactor NADH or NADPH of a keto compound of general formula I:

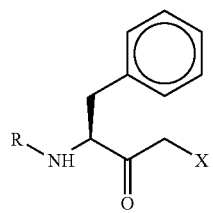

(I)

wherein R is any protective group for amino functions and X=Cl, CN, OH, Br, or F, to the hydroxy compound of general formula II (R,S-compound):

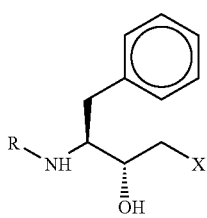

(II)

wherein R and X have the same meaning as in formula I, wherein the oxidoreductase is selected from the group consisting of:
(1) an isolated polypeptide having the amino acid sequence of SEQ ID NO:1; and
(2) isolated polypeptides having at least 75% amino acid sequence identity to SEQ ID NO:1 and enantiomeric selectivity of at least 80% toward the hydroxyl compound of general formula II.

19. An isolated oxidoreductase suitable for the enantioselective enzymatic reduction in the presence of a cofactor NADH or NADPH of a keto compound of general formula I:

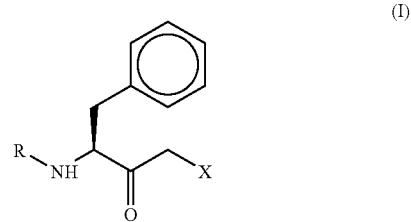

(I)

wherein R is any protective group for amino functions and X=Cl, CN, OH, Br, or F, to the hydroxy compound of general formula II (R,S-compound):

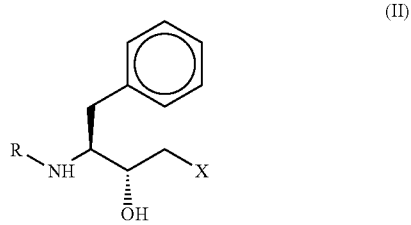

(II)

wherein R and X have the same meaning as in formula I, wherein the oxidoreductase is selected from the group consisting of:
(1) polypeptide which is encoded by the nucleic acid sequence SEQ ID NO:16, and
(2) polypeptides which are encoded by nucleic acid sequences which hybridize to a full length sequence of SEQ ID NO:16 when hybridization is carried out in a 0.7-1 M NaCl solution at 60° C. and washing is carried out with a 0.1 to 0.5-fold SSC solution at 65° C. and enantiomeric selectivity of at least 80% toward the hydroxyl compound of general formula II.

* * * * *

UNITED STATES PATENT AND TRADEMARK OFFICE
CERTIFICATE OF CORRECTION

PATENT NO. : 8,932,835 B2  
APPLICATION NO. : 12/680148  
DATED : January 13, 2015  
INVENTOR(S) : Gupta et al.

Page 1 of 1

It is certified that error appears in the above-identified patent and that said Letters Patent is hereby corrected as shown below:

IN THE SPECIFICATION

Column 8
Line 30, change "750 by" to --750 bp--

Column 9
Line 1, change "750 by" to --750 bp--
Line 62, change "400 by" to --400 bp--

Column 10
Line 51, change "750 by" to --750 bp--

Signed and Sealed this
Twenty-sixth Day of January, 2016

Michelle K. Lee
*Director of the United States Patent and Trademark Office*